(12) United States Patent
Krig et al.

(10) Patent No.: US 8,064,997 B2
(45) Date of Patent: *Nov. 22, 2011

(54) METHOD AND APPARATUS FOR TREATING IRREGULAR VENTRICULAR CONTRACTIONS SUCH AS DURING ATRIAL ARRHYTHMIA

(75) Inventors: David B. Krig, Brooklyn Park, MN (US); Jesse W. Hartley, Lino Lakes, MN (US); Wyatt Stahl, Vadnais Heights, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1045 days.

This patent is subject to a terminal disclaimer.

(21) Appl. No.: 11/423,516

(22) Filed: Jun. 12, 2006

(65) Prior Publication Data

US 2007/0016258 A1 Jan. 18, 2007

Related U.S. Application Data

(63) Continuation of application No. 09/316,515, filed on May 21, 1999, now Pat. No. 7,062,325.

(51) Int. Cl.
*A61N 1/362* (2006.01)
(52) U.S. Cl. ............................................................ 607/9
(58) Field of Classification Search .................. 607/4, 5, 607/9, 14
See application file for complete search history.

(56) References Cited

U.S. PATENT DOCUMENTS

| | | | |
|---|---|---|---|
| 3,857,399 A | 12/1974 | Zacouto | |
| 4,030,510 A | 6/1977 | Bowers | |
| 4,059,116 A | 11/1977 | Adams | |
| 4,163,451 A | 8/1979 | Lesnick et al. | |
| 4,208,008 A | 6/1980 | Smith | |
| RE30,387 E | 8/1980 | Denniston, III et al. | |
| 4,432,360 A | 2/1984 | Mumford et al. | |
| 4,503,857 A | 3/1985 | Boute et al. | |

(Continued)

FOREIGN PATENT DOCUMENTS

EP 0033418 8/1981
(Continued)

OTHER PUBLICATIONS

Metrix Model 3020 Implantable Atrial Defibrillator, Physician's Manual, InControl, Inc., Redmond, WA,(1998),pp. 4-24-4-27.

(Continued)

*Primary Examiner* — George Evanisko
(74) *Attorney, Agent, or Firm* — Schwegman, Lundberg & Woessner, P.A.

(57) ABSTRACT

A cardiac rhythm management system is capable of treating irregular ventricular heart contractions, such as during atrial tachyarrhythmias such as atrial fibrillation. A first indicated pacing interval is computed based at least partially on a most recent V-V interval duration between ventricular beats and a previous value of the first indicated pacing interval. Pacing therapy is provided based on either the first indicated pacing interval or also based on a second indicated pacing interval, such as a sensor-indicated pacing interval. A weighted averager such as an infinite impulse response (IIR) filter adjusts the first indicated pacing interval for sensed beats and differently adjusts the first indicated pacing interval for paced beats. The system regularizes ventricular rhythms by pacing the ventricle, but inhibits pacing when the ventricular rhythms are stable.

23 Claims, 14 Drawing Sheets

U.S. PATENT DOCUMENTS

| | | |
|---|---|---|
| 4,556,063 A | 12/1985 | Thompson et al. |
| 4,562,841 A | 1/1986 | Brockway et al. |
| 4,596,255 A | 6/1986 | Snell et al. |
| 4,791,936 A | 12/1988 | Snell et al. |
| 4,809,697 A | 3/1989 | Causey, III et al. |
| 4,830,006 A | 5/1989 | Haluska et al. |
| 4,869,252 A | 9/1989 | Gilli |
| 4,890,617 A | 1/1990 | Markowitz et al. |
| 4,905,697 A | 3/1990 | Heggs et al. |
| 4,917,115 A | 4/1990 | Flammang et al. |
| 4,920,965 A | 5/1990 | Funke et al. |
| 4,928,688 A | 5/1990 | Mower |
| 4,932,406 A | 6/1990 | Berkovits |
| 4,940,054 A | 7/1990 | Grevis et al. |
| 4,941,471 A | 7/1990 | Mehra |
| 4,944,298 A | 7/1990 | Sholder |
| 4,944,928 A | 7/1990 | Grill et al. |
| 4,945,909 A | 8/1990 | Fearnot et al. |
| 4,972,834 A | 11/1990 | Begemann et al. |
| 4,998,974 A | 3/1991 | Aker |
| 5,012,814 A | 5/1991 | Mills et al. |
| 5,042,480 A | 8/1991 | Hedin et al. |
| 5,085,215 A | 2/1992 | Nappholz et al. |
| 5,101,824 A | 4/1992 | Lekholm |
| 5,107,850 A | 4/1992 | Olive |
| 5,127,404 A | 7/1992 | Wyborny et al. |
| 5,129,394 A | 7/1992 | Mehra |
| 5,139,020 A | 8/1992 | Koestner et al. |
| 5,144,949 A | 9/1992 | Olson |
| 5,156,147 A | 10/1992 | Warren et al. |
| 5,156,154 A | 10/1992 | Valenta, Jr. et al. |
| 5,179,949 A | 1/1993 | Chirife |
| 5,183,040 A | 2/1993 | Nappholz et al. |
| 5,184,614 A | 2/1993 | Collins et al. |
| 5,188,106 A | 2/1993 | Nappholz et al. |
| 5,193,535 A | 3/1993 | Bardy et al. |
| 5,193,550 A | 3/1993 | Duffin |
| 5,197,467 A | 3/1993 | Steinhaus et al. |
| 5,207,219 A | 5/1993 | Adams et al. |
| 5,271,395 A | 12/1993 | Wahlstrand et al. |
| 5,282,836 A | 2/1994 | Kreyenhagen et al. |
| 5,284,491 A | 2/1994 | Sutton et al. |
| 5,292,339 A | 3/1994 | Stephens et al. |
| 5,292,341 A | 3/1994 | Snell |
| 5,311,874 A | 5/1994 | Baumann et al. |
| 5,312,452 A | 5/1994 | Salo |
| 5,331,966 A | 7/1994 | Bennett et al. |
| 5,334,220 A | 8/1994 | Sholder |
| 5,340,361 A | 8/1994 | Sholder |
| 5,350,409 A | 9/1994 | Stoop et al. |
| 5,356,425 A | 10/1994 | Bardy et al. |
| 5,360,437 A | 11/1994 | Thompson |
| 5,365,932 A | 11/1994 | Greenhut |
| 5,372,607 A | 12/1994 | Stone et al. |
| 5,376,106 A | 12/1994 | Stahmann et al. |
| 5,379,776 A | 1/1995 | Murphy et al. |
| 5,383,910 A | 1/1995 | den Dulk |
| 5,387,229 A | 2/1995 | Poore |
| 5,391,189 A | 2/1995 | van Krieken et al. |
| 5,395,373 A | 3/1995 | Ayers |
| 5,395,397 A | 3/1995 | Lindgren et al. |
| 5,400,796 A | 3/1995 | Wecke |
| 5,411,524 A | 5/1995 | Rahul |
| 5,411,531 A | 5/1995 | Hill et al. |
| 5,417,714 A | 5/1995 | Levine et al. |
| 5,423,869 A | 6/1995 | Poore et al. |
| 5,431,691 A | 7/1995 | Snell et al. |
| 5,437,285 A | 8/1995 | Verrier et al. |
| 5,462,060 A | 10/1995 | Jacobson et al. |
| 5,474,574 A | 12/1995 | Payne et al. |
| 5,480,413 A | 1/1996 | Greenhut et al. |
| 5,486,198 A | 1/1996 | Ayers et al. |
| 5,487,752 A | 1/1996 | Salo et al. |
| 5,507,782 A | 4/1996 | Kieval et al. |
| 5,507,784 A | 4/1996 | Hill et al. |
| 5,514,163 A | 5/1996 | Markowitz et al. |
| 5,522,850 A | 6/1996 | Yomtov et al. |
| 5,522,859 A | 6/1996 | Stroebel et al. |
| 5,523,942 A | 6/1996 | Tyler et al. |
| 5,527,347 A | 6/1996 | Shelton et al. |
| 5,534,016 A | 7/1996 | Boute |
| 5,540,232 A | 7/1996 | Laney et al. |
| 5,540,727 A | 7/1996 | Tockman et al. |
| 5,545,182 A | 8/1996 | Stotts et al. |
| 5,545,186 A | 8/1996 | Olson et al. |
| 5,549,649 A | 8/1996 | Florio et al. |
| 5,549,654 A | 8/1996 | Powell |
| 5,554,174 A | 9/1996 | Causey, III |
| 5,560,369 A | 10/1996 | McClure et al. |
| 5,560,370 A | 10/1996 | Verrier et al. |
| 5,562,711 A | 10/1996 | Yerich et al. |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. |
| 5,607,460 A | 3/1997 | Kroll et al. |
| 5,613,495 A | 3/1997 | Mills et al. |
| 5,620,471 A | 4/1997 | Duncan |
| 5,620,473 A | 4/1997 | Poore |
| 5,622,178 A | 4/1997 | Gilham |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,683,429 A | 11/1997 | Mehra |
| 5,690,689 A | 11/1997 | Sholder |
| 5,700,283 A | 12/1997 | Salo |
| 5,702,424 A | 12/1997 | Legay et al. |
| 5,713,928 A | 2/1998 | Bonnet et al. |
| 5,713,929 A | 2/1998 | Hess et al. |
| 5,713,930 A | 2/1998 | van der Veen et al. |
| 5,713,932 A | 2/1998 | Gillberg et al. |
| 5,716,382 A | 2/1998 | Snell |
| 5,716,383 A | 2/1998 | Kieval et al. |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,725,561 A | 3/1998 | Stroebel et al. |
| 5,730,141 A | 3/1998 | Fain et al. |
| 5,730,142 A | 3/1998 | Sun et al. |
| 5,738,096 A | 4/1998 | Ben-Haim |
| 5,741,304 A | 4/1998 | Patwardhan et al. |
| 5,741,308 A | 4/1998 | Sholder |
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,776,164 A | 7/1998 | Ripart |
| 5,776,167 A | 7/1998 | Levine et al. |
| 5,782,887 A | 7/1998 | van Krieken et al. |
| 5,788,717 A | 8/1998 | Mann et al. |
| 5,792,193 A | 8/1998 | Stoop |
| 5,800,464 A | 9/1998 | Kieval |
| 5,800,471 A | 9/1998 | Baumann |
| 5,814,077 A | 9/1998 | Sholder et al. |
| 5,814,081 A | 9/1998 | Ayers et al. |
| 5,814,085 A | 9/1998 | Hill |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,846,263 A | 12/1998 | Peterson et al. |
| 5,853,426 A | 12/1998 | Shieh |
| 5,855,593 A | 1/1999 | Olson et al. |
| 5,861,007 A | 1/1999 | Hess et al. |
| 5,865,838 A | 2/1999 | Obel et al. |
| 5,873,895 A | 2/1999 | Sholder et al. |
| 5,873,897 A | 2/1999 | Armstrong et al. |
| 5,891,178 A | 4/1999 | Mann et al. |

| | | |
|---|---|---|
| 5,893,882 A | 4/1999 | Peterson et al. |
| 5,897,575 A | 4/1999 | Wickham |
| 5,902,324 A | 5/1999 | Thompson et al. |
| 5,928,271 A | 7/1999 | Hess et al. |
| 5,931,856 A | 8/1999 | Bouhour et al. |
| 5,931,857 A | 8/1999 | Prieve et al. |
| 5,935,081 A | 8/1999 | Kadhiresan |
| 5,944,744 A | 8/1999 | Paul et al. |
| 5,951,592 A | 9/1999 | Murphy |
| 5,968,079 A | 10/1999 | Warman et al. |
| 5,974,341 A | 10/1999 | Er et al. |
| 5,978,707 A | 11/1999 | Krig et al. |
| 5,978,710 A | 11/1999 | Prutchi et al. |
| 5,983,138 A | 11/1999 | Kramer |
| 5,987,354 A | 11/1999 | Cooper et al. |
| 5,987,356 A | 11/1999 | DeGroot |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 6,026,320 A | 2/2000 | Carlson et al. |
| 6,041,251 A | 3/2000 | Kim et al. |
| 6,044,298 A | 3/2000 | Salo et al. |
| 6,047,210 A | 4/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,058,328 A | 5/2000 | Levine et al. |
| 6,081,745 A | 6/2000 | Mehra |
| 6,081,746 A | 6/2000 | Pendekanti et al. |
| 6,081,747 A | 6/2000 | Levine et al. |
| 6,081,748 A | 6/2000 | Struble et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,096,064 A | 8/2000 | Routh |
| 6,122,545 A | 9/2000 | Struble et al. |
| 6,128,529 A | 10/2000 | Elser |
| 6,129,745 A | 10/2000 | Sun et al. |
| 6,151,524 A | 11/2000 | Krig et al. |
| 6,223,072 B1 | 4/2001 | Mika et al. |
| 6,246,909 B1 | 6/2001 | Ekwall |
| 6,249,699 B1 | 6/2001 | Kim |
| 6,256,534 B1 | 7/2001 | Dahl |
| 6,263,242 B1 | 7/2001 | Mika et al. |
| 6,266,554 B1 | 7/2001 | Hsu et al. |
| 6,272,380 B1 | 8/2001 | Warman et al. |
| 6,280,391 B1 | 8/2001 | Olson et al. |
| 6,285,907 B1 * | 9/2001 | Kramer et al. ............ 607/9 |
| 6,292,693 B1 | 9/2001 | Darvish et al. |
| 6,317,632 B1 | 11/2001 | Krig et al. |
| 6,351,669 B1 | 2/2002 | Hartley et al. |
| 6,353,759 B1 | 3/2002 | Hartley et al. |
| 6,353,761 B1 | 3/2002 | Conley et al. |
| 6,408,209 B1 | 6/2002 | Bouhour et al. |
| 6,411,847 B1 | 6/2002 | Mower |
| 6,411,848 B2 | 6/2002 | Kramer et al. |
| 6,424,865 B1 | 7/2002 | Ding |
| 6,430,438 B1 | 8/2002 | Chen et al. |
| 6,434,424 B1 | 8/2002 | Igel et al. |
| 6,438,410 B2 | 8/2002 | Hsu et al. |
| 6,438,421 B1 | 8/2002 | Stahmann et al. |
| 6,501,987 B1 | 12/2002 | Lovett et al. |
| 6,501,988 B2 | 12/2002 | Kramer et al. |
| 6,512,951 B1 | 1/2003 | Marcovecchio et al. |
| 6,522,925 B1 | 2/2003 | Gilkerson et al. |
| RE38,119 E | 5/2003 | Mower |
| 6,687,541 B2 | 2/2004 | Marcovecchio et al. |
| 6,748,261 B1 | 6/2004 | Kroll et al. |
| 6,763,267 B2 | 7/2004 | Ding |
| 6,847,842 B1 | 1/2005 | Rodenhiser et al. |
| 6,957,100 B2 | 10/2005 | Vanderlinde et al. |
| 6,988,002 B2 * | 1/2006 | Kramer et al. ............ 607/18 |
| 7,039,461 B1 | 5/2006 | Lovett |
| 7,047,066 B2 | 5/2006 | Vanderlinde et al. |
| 7,062,325 B1 * | 6/2006 | Krig et al. ............ 607/14 |
| 7,069,077 B2 | 6/2006 | Lovett et al. |
| 7,120,490 B2 | 10/2006 | Chen et al. |
| 7,142,915 B2 | 11/2006 | Kramer et al. |
| 7,142,918 B2 | 11/2006 | Stahmann et al. |
| 7,181,278 B2 * | 2/2007 | Kramer et al. ............ 607/9 |
| 7,212,849 B2 | 5/2007 | Zhang et al. |
| 7,212,860 B2 * | 5/2007 | Stahmann et al. ............ 607/14 |
| 7,239,914 B2 | 7/2007 | Lovett et al. |
| 7,383,086 B2 | 6/2008 | Ding |
| 7,460,908 B2 | 12/2008 | Krig et al. |
| 7,680,530 B2 | 3/2010 | Vanderlinde et al. |
| 7,742,814 B2 | 6/2010 | Lovett |
| 7,805,192 B2 | 9/2010 | Stahmann et al. |
| 2002/0062139 A1 | 5/2002 | Ding |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0091415 A1 | 7/2002 | Lovett et al. |
| 2002/0120298 A1 | 8/2002 | Kramer et al. |
| 2003/0004551 A1 | 1/2003 | Chen et al. |
| 2003/0069610 A1 | 4/2003 | Kramer et al. |
| 2003/0078630 A1 | 4/2003 | Lovett et al. |
| 2003/0233131 A1 | 12/2003 | Kramer et al. |
| 2004/0010295 A1 | 1/2004 | Kramer et al. |
| 2004/0172076 A1 | 9/2004 | Stahmann et al. |
| 2004/0215249 A1 | 10/2004 | Corbucci |
| 2004/0215259 A1 | 10/2004 | Krig et al. |
| 2004/0243188 A1 | 12/2004 | Vanderlinde et al. |
| 2005/0038480 A1 | 2/2005 | Ding |
| 2007/0073348 A1 | 3/2007 | Stahmann et al. |
| 2007/0135853 A1 | 6/2007 | Kramer et al. |
| 2007/0233201 A1 | 10/2007 | Lovett et al. |
| 2007/0288062 A1 | 12/2007 | Stahmann et al. |
| 2009/0076563 A1 | 3/2009 | Krig et al. |
| 2010/0249866 A1 | 9/2010 | Lovett et al. |
| 2011/0015691 A1 | 1/2011 | Stahmann et al. |
| 2011/0087303 A1 | 4/2011 | Stahmann et al. |

FOREIGN PATENT DOCUMENTS

| | | |
|---|---|---|
| EP | 0360412 | 3/1990 |
| EP | 0401962 | 12/1990 |
| EP | 0597459 | 5/1994 |
| EP | 0617980 | 10/1994 |
| EP | 0748638 | 12/1996 |
| JP | 07-072910 A | 3/1995 |
| WO | WO-93/02746 | 2/1993 |
| WO | WO-95/09029 | 4/1995 |
| WO | WO-97/11745 | 4/1997 |
| WO | WO-98/48891 | 11/1998 |
| WO | WO-00/38782 | 7/2000 |
| WO | WO-00/71200 | 11/2000 |
| WO | WO-00/71203 | 11/2000 |
| WO | WO-0071200 A1 | 11/2000 |
| WO | WO-0071202 | 11/2000 |
| WO | WO-0071203 A1 | 11/2000 |

OTHER PUBLICATIONS

"French CNH Equipment Approvals", *Clinica*, 417, p. 9, (Sep. 5, 1990),3 pages.

"Harmony, Automatic Dual Chamber Pacemaker, Product Information and Programming Guide", *Viatron Medical*, 22 p., (Published Prior to Nov. 13, 2003), Harmony Dual Chamber mentioned in publication *Clinica*, 467, p. 16, Sep. 11, 1991, "Rate Devices Impact Pacemaker Market", also mentioned in *Clinica*, p. 9, Sep. 5, 1990 French CNH Equi, 22 p.

"Pacemaker System Guide for PULSAR MAX II; Mulitprogrammable Pacemakers", Product brochure published by Guidant Corporation,(Apr. 18, 1999),pp. 6-48 and 6-49.

"Pacemaker System Guide for PULSAR MAX II; Multiprogrammable Pacemakers", Product brochure published by Guidant Corporation,(Apr. 18, 1999),p. 6-39-6-51.

"Rate-Adaptive Devices Impact Pacemaker Market", *Clinica*, 467, p. 16, (Sep. 11, 1991),6 pages.

"Vitatron Medical Harmony Automatic Dual Chamber Pacemaker Product Information and Programming Guide", *Viatron Medical*, 22 p., (Date Unknown), Harmony Dual Chamber Harmony mentioned in publication *Clinica*, 467, p. 16, Sep. 11, 1991, "Rate Devices Impact Pacemaker Market", also mentioned in *Clinica*, 417, p. 9, Sep. 5, 1990 "French CNH Equipment Approvals"., Product Brochure published by Vitatron Medical,22 pgs.

Ayers, Gregory M., et al., "Ventricular Proarrhythmic Effects of Ventricular Cycle Length and Shock Strength in a Sheep Model of Transvenous Atrial Defibrillation", *Circulation*, 89 (1), (Jan. 1994),413-422.

Blommaert, D., et al., "Effective Prevention of Atrial Fibrillation by Continuous Atrial Overdrive Pacing After Coronary Artery Bypass Surgery", *JACC*, vol. 35, No. 6, (May 2000),pp. 1411-1415.

Buhr, Trina A., et al., "Novel Pacemaker Algorithm Diminishes Short-Coupled Ventricular Beats in Atrial Fibrillation", *PACE*, vol. 24, Part II, (Apr. 2001),729.

Campbell, R. M., et al., "Atrial Overdrive Pacing for Conversion of Atrial Flutter in Children", *Pediatrics*, 75(4), (Apr. 1985),730-736.

Clark, David M., et al., "Hemodynamic Effects of an Irregular Sequence of Ventricular Cycle Lengths During Atrial Fibrillation", *JACC*, vol. 30, No. 4, (Oct. 1997),1039-1045.

Duckers, H. J., et al., "Effective use of a novel rate-smoothing algorithm in atrial fibrillation by ventricular pacing", *European Heart Journal*, 18, (1997),pp. 1951-1955.

Fahy, G. J., et al., "Pacing Strategies to Prevent Atrial Fibrillation", *Atrial Fibrillation*, 14 (4), (Nov. 1996),pp. 591-596.

Fromer, M., et al., "Algorithm for the Prevention of Ventricular Tachycardia Onset: The Prevent Study", *The American Journal of Cardiology*, 83 (5B), (Mar. 11, 1999),pp. 45D-47D.

Garrigue, S., et al., "Prevention of Atrial Arrhythmias during DDD Pacing by Atrial Overdrive", *PACE*, vol. 21, (Sep. 1998),pp. 1751-1759.

Greenhut, S., et al., "Effectiveness of a Ventricular Rate Stabilization Algorithm During Atrial Fibrillation in Dogs", *Pace Abstract*, Abstract No. 60,(1996),1 p.

Guidant, "CONTAK TR CHFD Model 1241", *System Guide*, Congestive Heart Failure device,(1999),1-191.

Heuer, H., et al., "Dynamic Dual-Chamber Overdrive Pacing with an Implantable Pacemaker System: A New Method for Terminating Slow Ventricular Tachycardia", *Zeitschrift fur Kardiologie*, 75, German Translation by the Ralph McElroy Translation Company, Austin, TX,(1986),6 pages.

Heuer, H., et al., "Dynamische Zweikammer-Overdrive-Stimulation mit einem implantierbaren Schrittmachersystem als neue Methode zur Beendigung Langsamer ventrikularer Tachykardien", *Z Kardiol*; 75, Includes English translation (5 pgs.),(1986),pp. 673-675.

Jenkins, "Diagnosis of Atrial Fibrillation Using Electrogram from Chronic Leads: Evaluation of Computer Algorithm", *PACE*, 11, (1988),pp. 622-631.

Jung, J., et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998),pp. 689-695.

Krig, David B., "Method and Apparatus for Treating Irregular Ventricular Contractions Such As During Atrial Arrhythmia", U.S. Appl. No. 10/643,590, filed Aug. 19, 2003, 45 pgs.

Krig, David B., "Method and Apparatus for Treating Irregular Ventricular Contractions Such As During Atrial Arrhythmia", U.S. Appl. No. 10/852,602, filed on May 24, 2004, 60 pgs.

Lau, Chu-Pak, et al., "Efficacy of Ventricular Rate Stabilization by Right Ventricular Pacing During Atrial Fibrillation", *PACE*, vol. 21, (Mar. 1998),542-548.

Lovett, Eric, "Cardiac Pacing System for Prevention of Ventricular Fibrillation and Ventricular Tachycardia Episode", U.S. Appl. No. 09/569,295, filed May 13, 2000, 71 pgs.

Medtronic, "INSYNC III Device Model 8042", *Device Programming Guide*, INSYNC III Device Model 8042, Vision Programmer Software Model 9981,(2000),1-260.

Medtronic, "INSYNC III Device Model 8042", *Device Reference Guide*, INSYNC III Device Model 8042, Vision Programmer Software Model 9981,(2002),1-252.

Mehra, R., et al., "Prevention of Atrial Fibrillation/Flutter by Pacing Techniques", *Interventional Electrophysiology*, Second Edition, Chapter 34, Futura Publishing Company, Inc.,(1996(),pp. 521-540.

Morris, et al., "Intracardiac Electrogram Transformation: Morphometric Implications for Implantable Devices", *Journal of Electrocardiology*, 29 Supplement, (1996),pp. 124-129.

Mower, Morton, search results for U.S. Appl. No. 10/214,474, filed Aug. 8, 2002, entitled "Method and Apparatus for Treating Hemodynamic Disfunction", 3.

Murgatroyd, F. D., et al., "A new Pacing Algorithm for Overdrive Suppression of Atrial Fibrillation", *PACE*, vol. 17., (Nov. 1994, Part),pp. 1966-1973.

Rodenhiser, Kristen, "Method and Apparatus for Reducing Early Recurrence of Atrial Fibrillation with Defibrillation Shock Therapy", U.S. Appl. No. 09/570,645, filed May 15, 2000, 10 pgs.

Schuller, et al., "Far Field R-Wave Sensing—An Old Problem Repeating", *PACE*, 19, Part II, NASPE Abstract No. 1264,(1996),p. 631.

Seim, G., et al., "Classification of Atrial Flutter and Atrial Fibrillation Using an Atrial Dispersion Index (ADI)", *Guidant CRM Therapy Research Peer Review Report Revision 2.0*, (Jan. 6, 1999),27 p.

St. Jude Medical, "Atlas +HF Models V-343, V-341", *User's Manual*, Implantable Cardioverter-Defibrillator,(Sep. 2003),1-30.

St. Jude Medical, "Epic HF Model V-339", *User's Manual*, Implantable Cardioverter-Defibrillator,(Jul. 2002),1-26.

St. Jude Medical, "Model 3510 Programmer with Model 3307 Software", *Reference Manual*, For Atlas, Atlas+, Epic, Epic+, Photon u and Photon Implantable Cardioverter/Defibrillators,(Sep. 2003),1-314.

Stahmann, Jeffrey E., et al., "Apparatus and Method for Pacing Mode Switching During Atrial Tachyarrhythmias", U.S. Appl. No. 10/713,556, filed Nov. 13, 2003, 26 pgs.

Stephany, et al., "Real-Time Estimation of Magnitude-Square Coherence for Use in Implantable Devices", *IEEE Computers in Cardiology*, (1992),pp. 375-378.

Sutton, R., "Pacing in Atrial Arrhythmias", *PACE*, vol. 13, (Dec. 1990, Part),pp. 1823-1827.

Swiryn, S., et al., "Detection of Atrial Fibrillation by Pacemakers and Antiarrhythic Devices", *Nonpharmacological Management of Atrial Fibrillation*, Chapter 21, Future Publishing Co, Inc. Armond, NY,(1997),pp. 309-318.

Vanderlinde, Scott, et al., "Method and System for Display of Cardiac Event Intervals in a Resynchronization Pacemaker", U.S. Appl. No. 10/792,663, filed Mar. 3, 2004, 23 pgs.

Wittkampf, Fred H., et al., "Effect of Right Ventricular Pacing on Ventricular Rhythm During Atrial Fibrillation", *JACC*, vol. 11, No. 3, (Mar. 1988),539-545.

Wittkampf, F.H.M., et al., "Rate Stabilization by Right Ventricular Pacing in Patients with Atrial Fibrillation", *Pace*, vol. 9, Part II, (Nov.-Dec. 1986), 1147-1153.

Wittkampf, F.H.M., et al., "Rate Stabilization by Right Ventricular Patching in Patients with Atrial Fibrillation", *Pace*, 9, (Nov.-Dec. 1986),1147-1153.

Zhu, D. W., "Electrophysiology, Pacing and Arrhythmia—Pacing Therapy for Atrial Tachyarrhythmias", *Clinical Cardiology*, 19(9), (1996),737-742.

"U.S. Appl. No. 09/615,588, Notice of Allowance mailed Oct. 4, 2001", 4 pgs.

"U.S. Appl. No. 09/792,651, Non-Final Office action mailed Nov. 20, 2002", 10 pgs.

"U.S. Appl. No. 11/549,368, Notice of Allowance mailed Feb. 1, 2010", 6 pgs.

"European Application Serial No. 00936114.6, Communication mailed Sep. 15, 2004", 2 pgs.

"European Application Serial No. 00936114.6, Communication mailed Oct. 19, 2006", 2 pgs.

European Application Serial No. 00936114.6, Response filed Mar. 24, 2005 to Communication mailed Sep. 15, 2004, 23 pgs.

"European Application Serial No. 00936114.6, Response filed Apr. 30, 2007 to Communication mailed Oct. 19, 2006", 16 pgs.

"European Application Serial No. 01999174.4, Communication mailed Apr. 12, 2005", 4 pgs.

"European Application Serial No. 01999174.4, Communication mailed Apr. 21, 2009", 3 pgs.

"European Application Serial No. 01999174.4, Response filed Aug. 19, 2009 to Communication mailed on Apr. 21, 2009", 6 pgs.

"European Application Serial No. 01999174.4, Response filed Oct. 12, 2005 to Communication mailed Apr. 12, 2005", 10 pgs.

"International Application Serial No. PCT/US00/13835, International Preliminary Examination Report completed Aug. 20, 2001", 5 pgs.

"International Application Serial No. PCT/US00/13835, International Search Report mailed Oct. 2, 2000", 6 pgs.

"International Application Serial No. PCT/US00/13835, Written Opinion mailed Mar. 8, 2001", 5 pgs.

"International Application Serial No. PCT/US00/13838, Amendment filed May 9, 2001 in Response to Written Opinion mailed Feb. 14, 2001", 13 pgs.

"International Application Serial No. PCT/US00/13838, International Preliminary Examination Report completed Jul. 18, 2001", 15 pgs.

"International Application Serial No. PCT/US00/13838, Written Opinion mailed Feb. 14, 2001", 8 pgs.

"International Application Serial No. PCT/US00/13863, Amendment filed Jun. 12, 2001 in Response to Written Opinion mailed Mar. 14, 2001", 12 pgs.

"International Application Serial No. PCT/US00/13863, International Preliminary Examination Report completed Aug. 24, 2001", 12 pgs.

"International Application Serial No. PCT/US00/13863, International Search Report mailed Oct. 2, 2000", 3 pgs.

"International Application Serial No. PCT/US00/13863, Written Opinion mailed Mar. 14, 2001", 7 pgs.

"International Application Serial No. PCT/US00/13877, Amendment filed Jul. 26, 2001 in Response to Written Opinion", 11 pgs.

"International Application Serial No. PCT/US00/13877, International Preliminary Examination Report completed Aug. 30, 2001", 15 pgs.

"International Application Serial No. PCT/US00/13877, International Search Report mailed Oct. 2, 2000", 4 pgs.

"International Application Serial No. PCT/US00/13877, Written Opinion mailed May 28, 2001", 9 pgs.

"International Application Serial No. PCT/US01/49660, International Preliminary Examination Report completed Dec. 19, 2002", 2 pgs.

"International Application Serial No. PCT/US01/49660, International Search Report mailed Oct. 1, 2002", 8 pgs.

"International Application Serial No. PCT/US01/49660, Written Opinion mailed Oct. 1, 2002", 2 pgs.

"Japanese Application Serial No. 2000-619502, Notice of Reasons for Rejection mailed Mar. 25, 2008", (w/ English Translation), 5 pgs.

"Japanese Application Serial No. 2000-619502, Response and Amendment Claims filed Jun. 11, 2008 to Notice of Reasons for Rejection mailed Mar. 25, 2008", (w/ English Translation of Amended Claims), 14 pgs.

"Partial Prosecution File History for U.S. Appl. No. 11/673,098, filed Feb. 9, 2007", 36 pgs.

"Partial Prosecution File History for U.S. Appl. No. 11/733,332, filed Apr. 10, 2007", 37 pgs.

"Prosecution File History for U.S. Appl. No. 09/316,515, filed May 21, 1999", (issued as US 7,062,325), 176 pgs.

"Prosecution File History for U.S. Appl. No. 09/316,588, filed May 21, 1999", (issued as US 6,285,907), 29 pgs.

"Prosecution File History for U.S. Appl. No. 09/316,682, filed May 21, 1999", (issued as US 6,351,669), 23 pgs.

"Prosecution File History for U.S. Appl. No. 09/316,741, filed May 21, 1999", (issued as US 6,430,438), 51 pgs.

"Prosecution File History for U.S. Appl. No. 09/569,295, filed May 13, 2000", (issued as US 7,039,461), 111 pgs.

"Prosecution File History for U.S. Appl. No. 09/579,951, filed May 26, 2000", (issued as US 6,501,987), 48 pgs.

"Prosecution File History for U.S. Appl. No. 09/661,875, filed Sep. 14, 2000", (issued as US 6,512,951), 24 pgs.

"Prosecution File History for U.S. Appl. No. 09/693,402, filed Oct. 20, 2000", (issued as US 6,353,759), 18 pgs.

"Prosecution File History for U.S. Appl. No. 09/748,358, filed Dec. 26, 2000", (issued as US 6,501,988), 7 pgs.

"Prosecution File History for U.S. Appl. No. 09/748,724, filed Dec. 26, 2000", (issued as US 6,957,100), 46 pgs.

"Prosecution File History for U.S. Appl. No. 09/748,796, filed Dec. 26, 2000", (issued as US 7,142,918), 63 pgs.

"Prosecution File History for U.S. Appl. No. 09/751,431, filed Dec. 29, 2000", 46 pgs.

"Prosecution File History for U.S. Appl. No. 09/837,019, filed Apr. 18, 2001", (issued as US 6,411,848), 18 pgs.

"Prosecution File History for U.S. Appl. No. 10/017,800, filed Dec. 12, 2001", (issued as US 7,239,914), 202 pgs.

"Prosecution File History for U.S. Appl. No. 10/054,427, filed Jan. 22, 2002", (issued as US 6,763,267), 22 pgs.

"Prosecution File History for U.S. Appl. No. 10/211,414, filed Aug. 2, 2002", (issued as US 7,120,490), 59 pgs.

"Prosecution File History for U.S. Appl. No. 10/304,149, filed Nov. 25, 2002", (issued as US 6,988,002), 25 pgs.

"Prosecution File History for U.S. Appl. No. 10/306,514, filed Nov. 27, 2002", (issued as US 7,069,077), 18 pgs.

"Prosecution File History for U.S. Appl. No. 10/334,397, filed Dec. 30, 2002", (issued as US 6,687,541), 24 pgs.

"Prosecution File History for U.S. Appl. No. 10/394,497, filed Mar. 20, 2003", (issued as US 7,181,278), 29 pgs.

"Prosecution File History for U.S. Appl. No. 10/462,029, filed Jun. 13, 2003", (issued as US 7,142,915), 15 pgs.

"Prosecution File History for U.S. Appl. No. 10/713,556, filed Nov. 13, 2003", (issued as US 7,212,860), 28 pgs.

"Prosecution File History for U.S. Appl. No. 10/792,663, filed Mar. 3, 2004", (issued as US 7,047,066), 11 pgs.

"Prosecution File History for U.S. Appl. No. 10/852,602, filed May 24, 2004", (issued as US 7,460,908), 97 pgs.

"Prosecution File History for U.S. Appl. No. 10/889,354, filed Jul. 12, 2004", 26 pgs.

"Prosecution File History for U.S. Appl. No. 11/380,148, filed Apr. 25, 2006", 47 pgs.

"Prosecution File History for U.S. Appl. No. 11/381,462, filed May 3, 2006", (issued as US 7,680,530), 33 pgs.

Cohen, R. J., et al., "Quantitative Model for Ventricular Response During Atrial Fibrillation", *IEEE Transactions on Biomedical Engineering*, 30, (1983), 769-782.

Lau, C. P., et al., "A new pacing method for rapid regularization and rate control in atrial fibrillation", *Am J Cardiol.*, 65(18), (May 15, 1990), 1198-1203.

Sweeney, M. O., et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction", *Circulation*, 107(23), (Jun. 17, 2003), 2932-2937.

Tse, H. F., et al., "Effects of ventricular rate regularization pacing on quality of life and symptoms in patients with atrial fibrillation (Atrial fibrillation symptoms mediated by pacing to mean rates [AF Symptoms study])", *Am J Cardiol.*, 94(7), (Oct. 2004), 938-41.

"U.S. Appl. No. 10/107,800, Supplemental Amendment & Response filed May 9, 2005 to Advisory Action mailed Apr. 21, 2005 and Final Office Action mailed Feb. 8, 2005", 14 pgs.

"U.S. Appl. No. 10/852,602, Amendment and Response filed Dec. 22, 2006 to Non-Final Office Action mailed Dec. 24, 2006", 20 pgs.

"U.S. Appl. No. 11/673,098 Final Office Action mailed Oct. 4, 2010", 9 pgs.

"U.S. Appl. No. 11/673,098, Response filed Jun. 24, 2010 to Non Final Office Action mailed Mar. 24, 2010 t", 8 pgs.

"U.S. Appl. No. 11/733,332 Notice of Allowance mailed Jul. 14, 2010", 7 pgs.

"U.S. Appl. No. 11/759,354, Non Final Office Action mailed Dec. 10, 2010", 11 pgs.

"European Application Serial No. 00936114.8, Summons to Attend Oral Proceedings mailed Jun. 23, 2010", 2.

"European Application No. 00936114.8, Response to Summons to Attend Oral Proceedings Filed Nov. 15, 2010", 10 pgs.

"European Application Serial No. 10153647.2, European Search Report mailed Apr. 26, 2010", 5 Pgs.

"European Application Serial No. 10153647.2, Office Action mailed on Jun. 14, 2010", 5 pgs.

Wittkampf, F H, et al., "Rate Stabilization by Right Ventricular Pachingin Patients With Atrial Fibrillationin Patients With Atrial Fibrillation Stabilisation de la Frequnce Cardiaque Par Stimulation Ventriculaire Chez Les Patients Porteurs de Fibrillation Auriculaive", Pace, XX, XX, vol. 9, No. 6, Part 2, 1147-1153, XP000562479 ISSN: 0147-8389, (Nov. 1, 1986), 1147-1153.

"U.S. Appl. No. 09/316,515, Final Office Action mailed Jul. 23, 2001", 9 pgs.

"U.S. Appl. No. 09/316,515, Final Office Action mailed Jul. 29, 2003", 6 pgs.

"U.S. Appl. No. 09/316,515, Final Office Action mailed Aug. 8, 2002", 9 pgs.

"U.S. Appl. No. 09/316,515, Non Final Office Action mailed Feb. 12, 2003", 7 pgs.

"U.S. Appl. No. 09/316,515, Non Final Office Action mailed Feb. 28, 2002", 11 pgs.

"U.S. Appl. No. 09/316,515, Non Final Office Action mailed Mar. 1, 2005", 15 pgs.

"U.S. Appl. No. 09/316,515, Non Final Office Action mailed Aug. 30, 2000", 8 pgs.

"U.S. Appl. No. 09/316,515, Notice of allowance mailed Aug. 12, 2003", 7 pgs.

"U.S. Appl. No. 09/316,515, Notice of allowance mailed Sep. 23, 2004", 8 pgs.

"U.S. Appl. No. 09/316,515, Response filed Jan. 30, 2001 to Non Final Office Action mailed Aug. 30, 2000", 20 pgs.

"U.S. Appl. No. 09/316,515, Response filed May 6, 2003 to Non Final Office Action mailed Feb. 12, 2003", 19 pgs.

"U.S. Appl. No. 09/316,515, Response filed May 28, 2002 to Non Final Office Action mailed Feb. 28, 2002", 6 pgs.

"U.S. Appl. No. 09/316,515, Response filed Jun. 7, 2001 to Final Office Action mailed Mar. 2, 2001", 8 pgs.

"U.S. Appl. No. 09/316,515, Response filed Jun. 30, 2004 to Non Final Office Action mailed Mar. 1, 2005", 19 pgs.

"U.S. Appl. No. 09/316,515, Response filed Nov. 6, 2001 to Final Office Action mailed Jul. 23, 2001", 6 pgs.

"U.S. Appl. No. 09/316,515, Response filed Dec. 9, 2002 to Final Office Action mailed Aug. 8, 2002", 8 pgs.

"U.S. Appl. No. 09/751,431, Final Office Action mailed Jan. 13, 2003", 10 pgs.

"U.S. Appl. No. 09/751,431, Non Final Office Action mailed Jul. 3, 2002", 14 pgs.

"U.S. Appl. No. 09/751,431. Response filed Apr. 14, 2003 to Final Office Action mailed Jan. 13, 2003", 8 pgs.

"U.S. Appl. No. 09/751,431. Response filed Nov. 4, 2002 to Non Final Office Action mailed Jul. 3, 2002", 11 pgs.

"U.S. Appl. No. 10/792,663, Preliminary Amendment filed Jul. 26, 2004", 5 pgs.

"U.S. Appl. No. 11/673,098, Response filed Feb. 3, 2011 to Final Office Action mailed Oct. 4, 2010", 9 pgs.

"U.S. Appl. No. 11/759,394, Response filed Mar. 10, 2011 to Non Final Office Action mailed Feb. 10, 2010", 12 pgs.

"U.S. Appl. No. 12/891,669, Notice of Allowance mailed Apr. 5, 2011", 6 pgs.

"U.S. Appl. No. 12/891,669, Response filed Mar. 15, 2011 to Non Final Office Action mailed Dec. 15, 2010", 7 pgs.

"European Application Serial No. 00936114.8, Rule 71(3) re: Approval of Text/Translation/Grant & Print Fees mailed Jan. 5, 2011", 67.

* cited by examiner

METHOD AND APPARATUS FOR TREATING IRREGULAR VENTRICULAR CONTRACTIONS SUCH AS DURING ATRIAL ARRHYTHMIA

CROSS REFERENCE TO RELATED APPLICATIONS

This application is a continuation of U.S. patent application Ser. No. 09/316,515, filed on May 21, 1999, now issued as U.S. Pat. No. 7,062,325, the specification of which is incorporated herein by reference.

This application is related to the following commonly assigned patent applications: "Cardiac Rhythm Management System Promoting Atrial Pacing," U.S. patent application Ser. No. 09/316,682, filed on May 21, 1999, now issued as U.S. Pat. No. 6,351,669; "Cardiac Rhythm Management System With Atrial Shock Timing Optimization," U.S. patent application Ser. No. 09/316,741, filed on May 21, 1999, now issued as U.S. Pat. No. 6,430,438; and "System Providing Ventricular Pacing and Biventricular Coordination," U.S. patent application Ser. No. 09/316,588, filed on May 21, 1999, now issued as U.S. Pat. No. 6,285,907; the disclosures of which are incorporated herein by reference.

TECHNICAL FIELD

The present system relates generally to cardiac rhythm management systems and particularly, but not by way of limitation, to a method and apparatus for treating irregular ventricular contractions, such as during an atrial arrhythmia.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the proper treatment of ventricular arrhythmias that are caused by atrial tachyarrhythmias such as atrial fibrillation. Atrial fibrillation is a common cardiac arrhythmia which reduces the pumping efficiency of the heart, though not to as great a degree as in ventricular fibrillation. However, this reduced pumping efficiency requires the ventricle to work harder, which is particularly undesirable in sick patients that cannot tolerate additional stresses. As a result of atrial fibrillation, patients may be required to limit their activity and exercise.

Although atrial fibrillation, by itself, is usually not life-threatening, prolonged atrial fibrillation may be associated with strokes, which are thought to be caused by blood clots forming in areas of stagnant blood flow. Treating such blood clots requires the use of anticoagulants. Atrial fibrillation may also cause pain, dizziness, and other irritation to the patient.

An even more serious problem, however, is that atrial fibrillation may induce irregular ventricular heart rhythms by processes that are yet to be fully understood. Such induced ventricular arrhythmias compromise pumping efficiency even more drastically than atrial arrhythmias. For these and other reasons, there is a need for a method and apparatus for treating irregular ventricular contractions during atrial arrhythmias such as atrial fibrillation.

SUMMARY OF THE INVENTION

The present system provides a method and apparatus for treating irregular ventricular contractions, such as during atrial arrhythmias (e.g., atrial fibrillation), or otherwise. The present system provides many advantages. Among other things, it is capable of treating irregular ventricular heart contractions, such as during atrial tachyarrhythmias. It provides a first indicated pacing rate that increases for sensed ventricular beats and decreases for paced ventricular beats. The system delivers more pacing during irregular sensed beats (such as during atrial tachyarrhythmias including atrial fibrillation or the like) and less pacing when sensed beats are regular. In a stable heart, the first indicated pacing rate is typically less than the intrinsic heart rate. This avoids unnecessary pacing of the heart when heart rhythms are substantially stable, allowing the heart to beat normally and at its own intrinsic heart rate.

One aspect of the system permits it to avoid rapid changes in heart rate, and to keep heart rate within acceptable upper and lower limits. The system allows the rate to become more regular and to approach a stable rhythm. This provides improved comfort of the patient experiencing irregular ventricular contractions. In a further embodiment, the system includes a second indicated pacing rate, such as a sensor-indicated rate, and provides pacing therapy based on both the first and second indicated pacing rates. Other aspects of the invention will be apparent on reading the following detailed description of the invention and viewing the drawings that form a part thereof.

In one embodiment, the system obtains V-V intervals between ventricular beats. A first indicated pacing interval is computed based at least partially on a most recent V-V interval duration and a previous value of the first indicated pacing interval. Pacing therapy is provided based on the first indicated pacing interval.

In a further embodiment, the first indicated pacing interval is adjusted by an amount based at least on the most recent V-V interval duration and the previous value of the first indicated pacing interval, if the most recent V-V interval is concluded by an intrinsic beat. If, however, the most recent V-V interval is concluded by a paced beat, then the first indicated pacing interval is increased by an amount based at least on the most recent V-V interval duration and the previous value of the first indicated pacing interval.

In another embodiment, the system detects an atrial tachyarrhythmia. The system obtains V-V intervals between ventricular beats. A first indicated pacing interval is computed based at least partially on a most recent V-V interval duration and a previous value of the first indicated pacing interval. Pacing therapy is provided based on the first indicated pacing interval, if the atrial tachyarrhythmia is present.

One embodiment provides a cardiac rhythm management system that includes, among other things, a ventricular sensing circuit, a controller, and a ventricular therapy circuit. The controller includes a V-V interval timer, a first register, for storing information associated with a first indicated pacing interval, and a filter that updates the first indicated pacing interval based on the V-V interval timer and the information stored in the first register. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
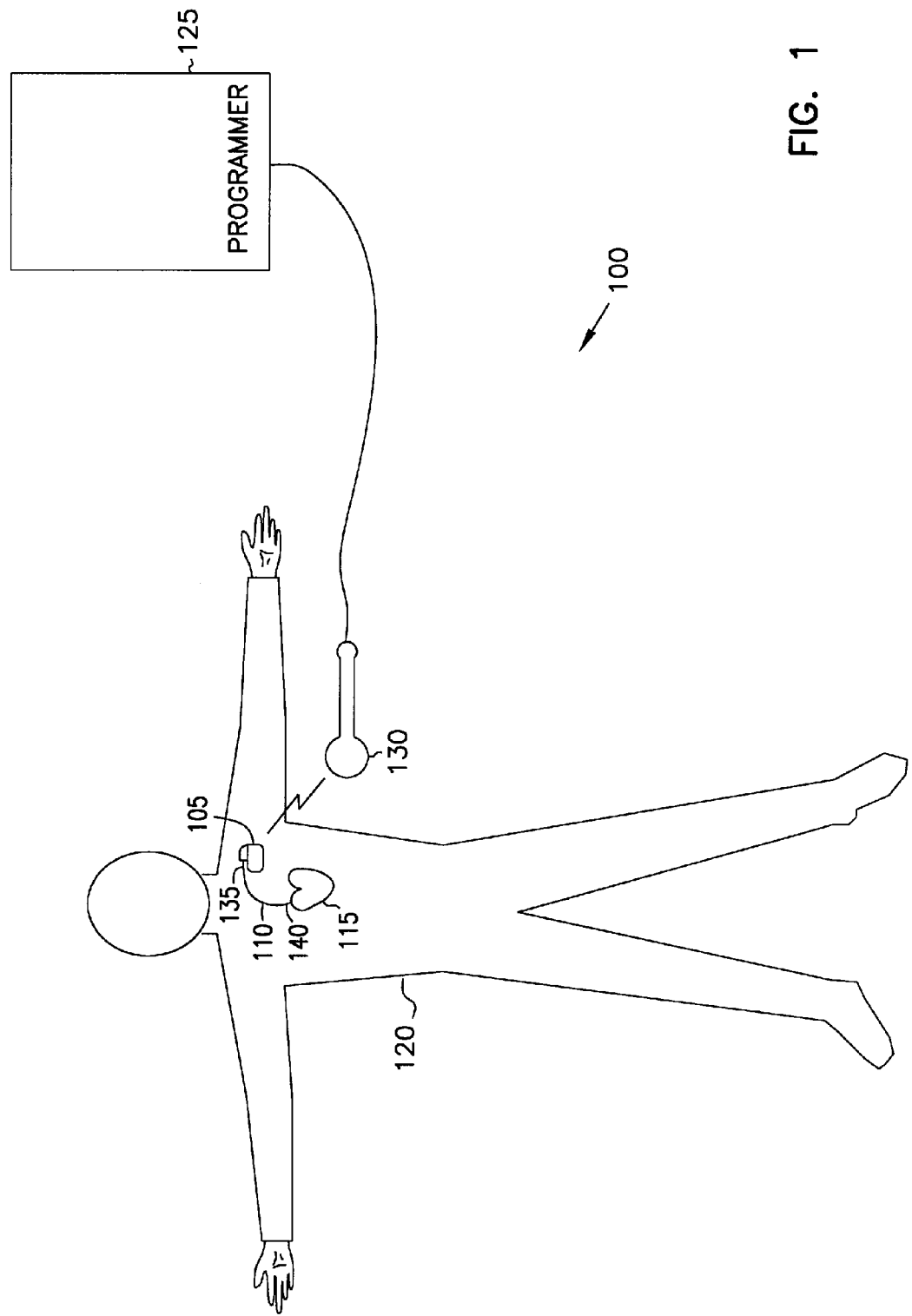
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

The present methods and apparatus will be described in applications involving implantable medical devices including, but not limited to, implantable cardiac rhythm management systems such as pacemakers, cardioverter/defibrillators, and pacer/defibrillators. However, it is understood that the present methods and apparatus may be employed in unimplanted devices, including, but not limited to, external pacemakers, cardioverter/defibrillators, pacer/defibrillators, monitors, programmers and recorders.

Problems Associated with Atrial Arrhythmias

As stated earlier, one potential cause of irregularity of ventricular contractions arises during atrial tachyarrhythmias, such as atrial fibrillation. During atrial fibrillation, irregular ventricular contractions may be caused by a conducted atrial tachyarrhythmia, then pacing the ventricle will regularize the ventricular heart rate by establishing retrograde conduction from the ventricle. This, in turn, is believed to block forward conduction of atrial signals through the atrioventricular (A-V) node. As a result, irregular atrial signals do not trigger resulting irregular ventricular contractions.

One therapy for treating irregular ventricular contractions during atrial fibrillation is to increase the ventricular heart rate by pacing the ventricle at a higher rate than the unpaced (intrinsic) ventricular heart rate. Such therapy is believed to decrease the discomfort experienced by the patient having atrial arrhythmia because it regulates the ventricular contractions to avoid short periods between contractions and/or long periods without a contraction. Such therapy is also believed to decrease the ability of the atrial fibrillation to induce irregular ventricular contractions.

An increase in rate of ventricular contractions, however, must be done carefully to avoid pacing the heart at an unnecessarily high rate. Furthermore, such a therapy should not impose pacing where normal or "intrinsic" heart pacing is adequate such as, for example, when atrial tachyarrhythmias no longer cause disorder of ventricular contractions. As long as the heart is actively paced, it may be difficult or impossible to determine when to cease such a therapy. One advantage of the present system is that it allows intrinsic ventricular rhythms, if such rhythms are regular, but provides pacing that stabilizes ventricular rhythms if they become irregular, as discussed below.

General System Overview and Examples

This document describes, among other things, a cardiac rhythm management system providing a method and apparatus for treating irregular ventricular contractions during atrial arrhythmia. FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
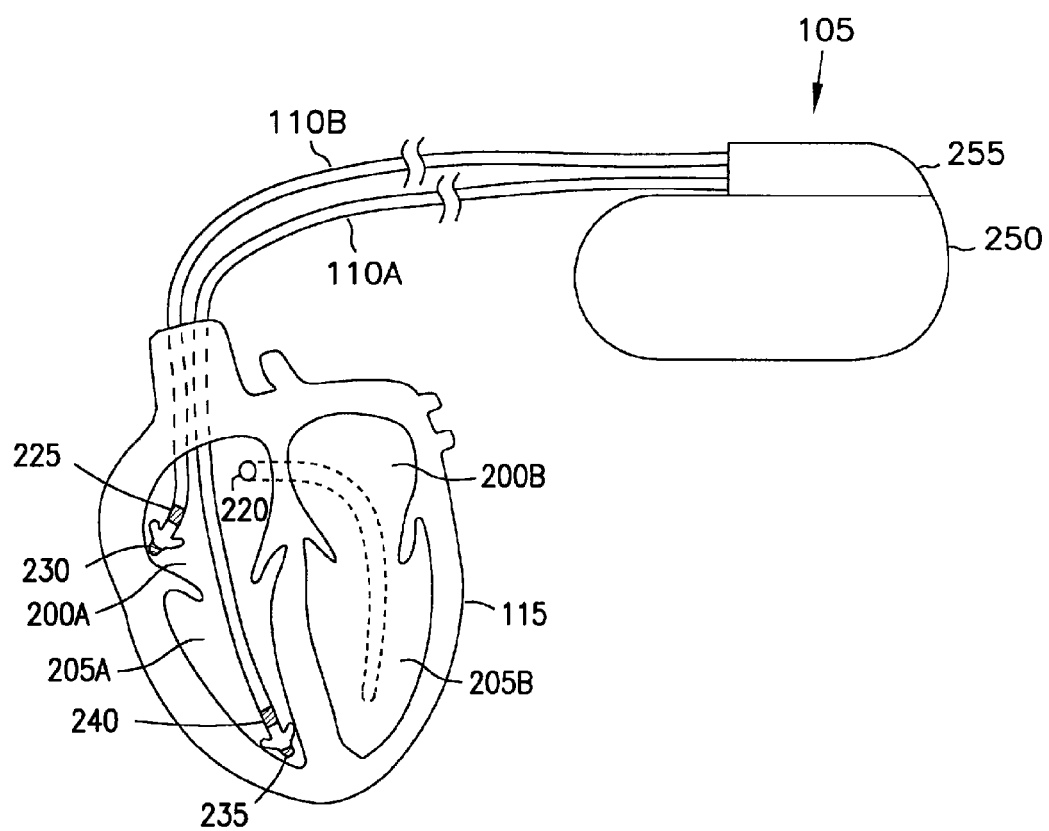
FIG. 2 is a schematic drawing illustrating one embodiment of a cardiac rhythm management device coupled by leads to a heart.

FIG. 2 is a schematic drawing illustrating, by way of example, but not by way of limitation, one embodiment of device 105 coupled by leads 110A-B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Example Cardiac Rhythm Management Device

Figure 3:
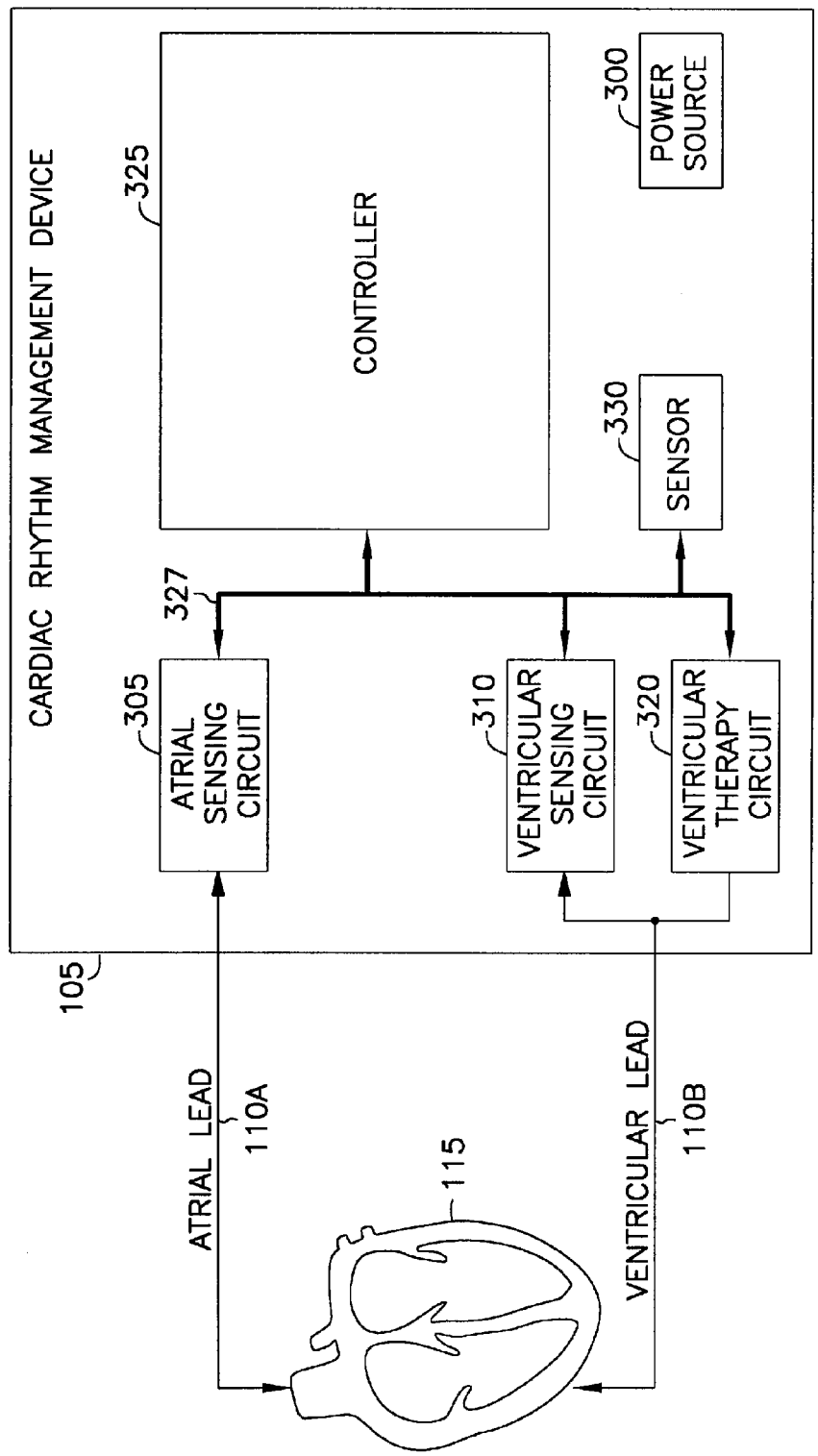
FIG. 3 is a schematic diagram illustrating generally one embodiment of portions of a cardiac rhythm management device coupled to a heart.

FIG. 3 is a schematic diagram illustrating generally, by way of example, but not by way of limitation, one embodiment of portions of device 105, which is coupled to heart 115. Device 105 includes a power source 300, an atrial sensing circuit 305, a ventricular sensing circuit 310, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of atrial fibrillation.

Ventricular sensing circuit 310 is coupled by ventricular lead 10B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 310 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles 205 of heart 115 for obtaining resulting evoked ventricular depolarizations. In one embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by ventricular therapy circuit 320 and/or other circuits, based on heart activity signals received from atrial sensing circuit 305 and ventricular sensing circuit 310, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 310 sense electrical signals from heart tissue in contact with the catheter leads 110A-B to which these sensing circuits 305 and 310 are coupled. Sensing circuits 305 and 310 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A-B. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Figure 4:
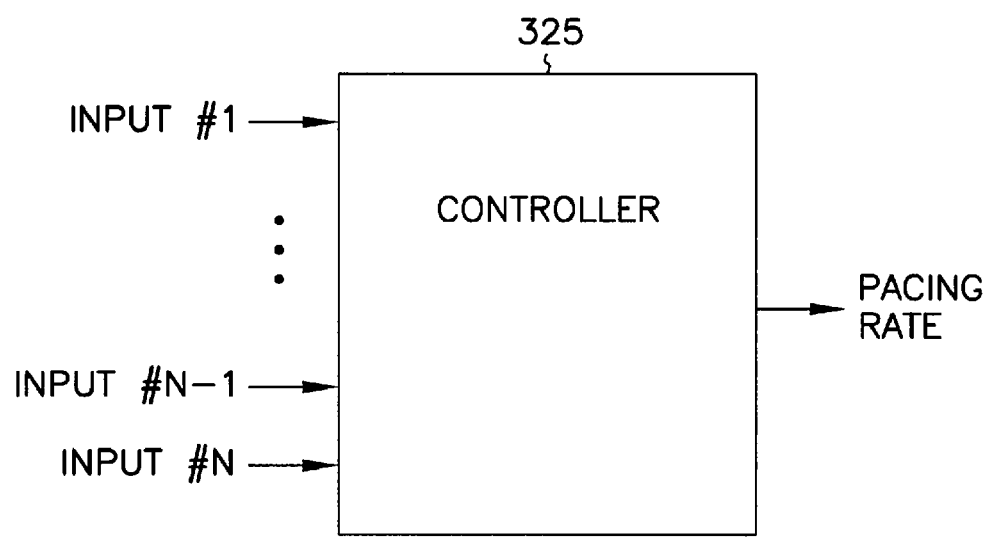
FIG. 4 is a schematic diagram illustrating generally one embodiment of a controller.

FIG. 4 is a schematic diagram illustrating generally, by way of example, but not by way of limitation, one embodiment of controller 325 that includes several different inputs to modify the rate at which pacing or other therapy is delivered. For example, Input #1 may provide information about left ventricular rate, Input #2 may provide an accelerometer-based indication of activity, and Input #3 may provide an impedance-based indication of respiration, such as minute ventilation. Based on at least one of these and/or other inputs, controller 325 provides an output indication of pacing rate as a control signal delivered to a therapy circuit, such as to ventricular therapy circuit 320. Ventricular therapy circuit 320 issues pacing pulses based on one or more such control signals received from controller 325. Control of the pacing rate may be performed by controller 325, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device 105.

Controller Example 1

Figure 5:
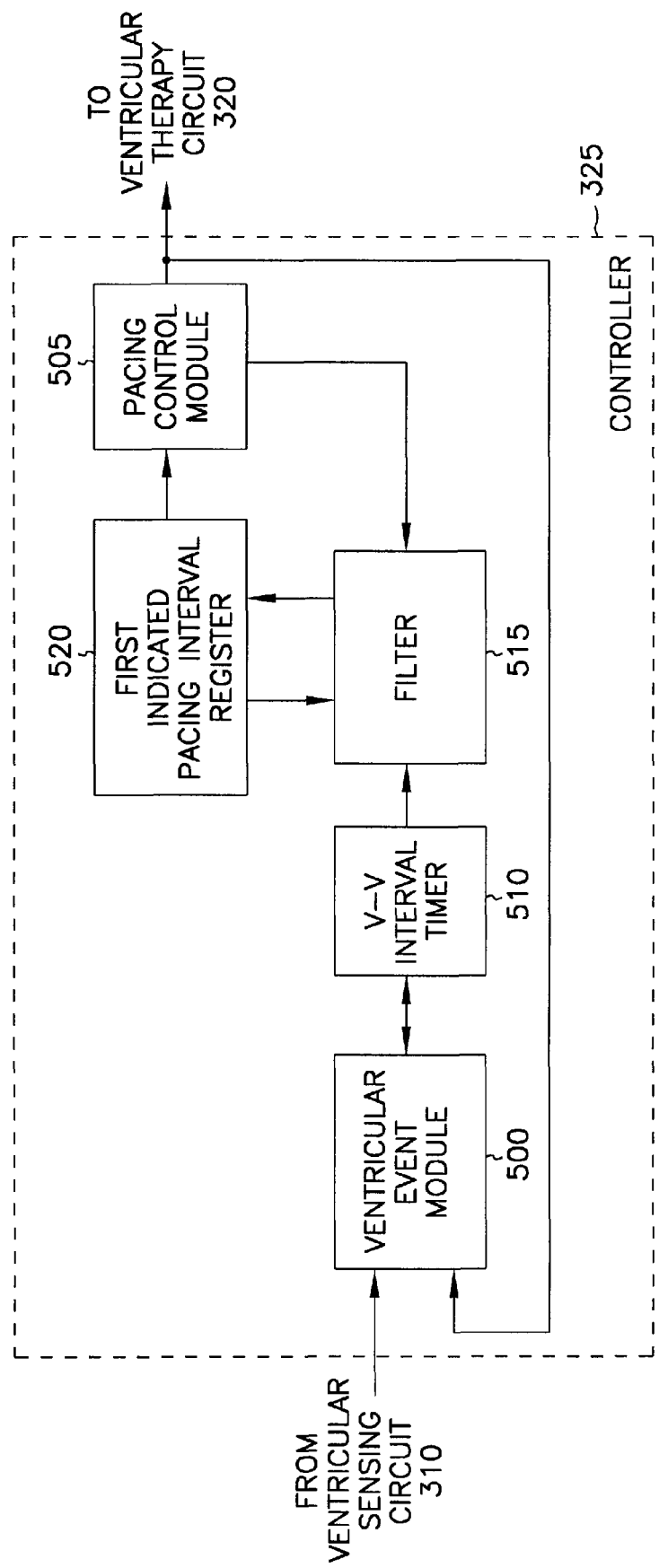
FIG. 5 is a schematic diagram illustrating generally one conceptualization of portions of a controller.

FIG. 5 is a schematic diagram illustrating generally, by way of example, but not by way of limitation, one conceptualization of portions of controller 325. At least one signal from ventricular sensing circuit 310 is received by ventricular event module 500, which recognizes the occurrence of ventricular events included within the signal. Such events are also referred to as "beats," "activations," "depolarizations," "QRS complexes," "R-waves," "contractions." Ventricular event module 500 detects intrinsic events (also referred to as sensed events) from the signal obtained from ventricular sensing circuit 310. Ventricular event module 500 also detects evoked events (resulting from a pace) either from the signal obtained from ventricular sensing circuit 310, or preferably from a ventricular pacing control signal obtained from pacing control module 505, which also triggers the delivery of a pacing stimulus by ventricular therapy circuit 320. Thus, ventricular events include both intrinsic/sensed events and evoked/paced events.

A time interval between successive ventricular events, referred to as a V-V interval, is recorded by a first timer, such as V-V interval timer 510. A filter 515 computes a "first indicated pacing interval," i.e., one indication of a desired time interval between ventricular events or, stated differently, a desired ventricular heart rate. The first indicated pacing interval is also referred to as a ventricular rate regularization (VRR) indicated pacing interval. In various embodiments, filter 515 includes an averager, a weighted averager, a median filter, an infinite (IIR) filter, a finite impulse response (FIR) filter, or any other analog or digital signal processing circuit providing the desired signal processing described more particularly below.

In one embodiment, filter 515 computes a new value of the first indicated pacing interval based on the duration of the most recent V-V interval recorded by timer 510 and on a previous value of the first indicated pacing interval stored in first indicated pacing interval register 520. Register 520 is then updated by storing the newly computed first indicated pacing interval in register 520. Based on the first indicated pacing interval stored in register 520, pacing control module 505 delivers control signals to ventricular therapy circuit 320 for delivering therapy, such as pacing stimuli, at the VRR-indicated ventricular heart rate corresponding to the inverse of the duration of the first indicated pacing interval.

Filter Example 1

In general terms, for one embodiment, device 105 obtains V-V intervals between successive sensed or evoked ventricular beats. Device 105 computes a new first indicated pacing interval based at least in part on the duration of the most recent V-V interval and a previous value of the first indicated pacing interval. Device 105 provides pacing therapy delivered at a rate corresponding to the inverse of the duration of the first indicated pacing interval.

Figure 6:
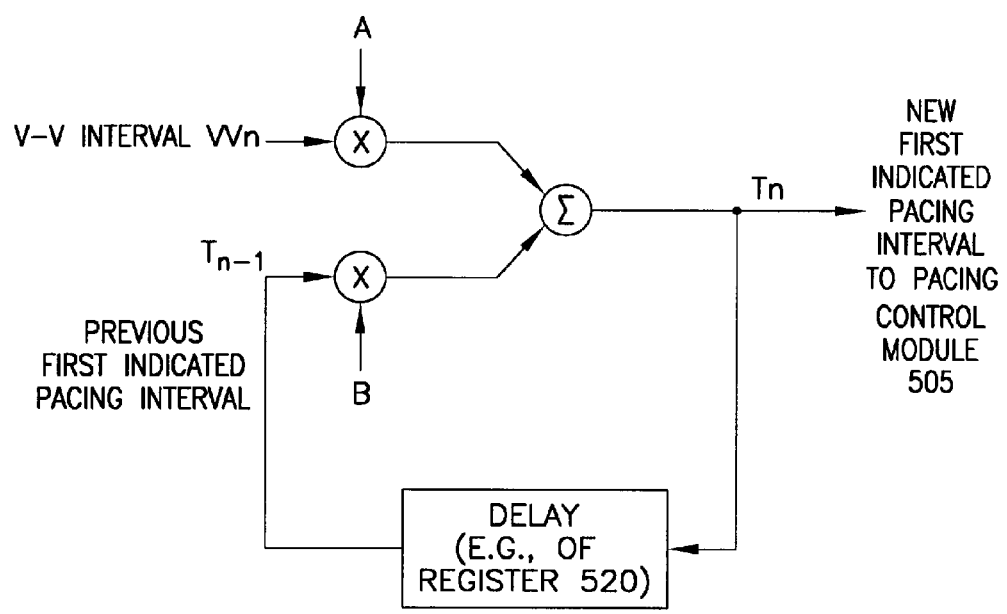
FIG. 6 is a signal flow diagram illustrating generally one conceptual embodiment of operating a filter.

FIG. 6 is a signal flow diagram illustrating generally, by way of example, but not by way of limitation, one embodiment of operating filter 515. Upon the occurrence of a sensed or evoked ventricular beat, timer 510 provides filter 515 with the duration of the V-V interval concluded by that beat, which is referred to as the most recent V-V interval ($VV_n$). Filter 515 also receives the previous value of the first indicated pacing interval ($T_{n-1}$) stored in register 520. The most recent V-V interval $VV_n$ and the previous value of the first indicated pacing interval $T_{n-1}$ are each scaled by respective constants A and B, and then summed to obtain a new value of the first indicated pacing interval ($T_n$), which is stored in register 520 and provided to pacing control module 505. In one embodiment, the coefficients A and B are different values, and are either programmable, variable, or constant.

If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$. In one embodiment, operation of the filter is described by $T_n = A \cdot VV_n + B \cdot T_{n-1}$, where A and B are coefficients (also referred to as "weights"), $VV_n$ is the most recent V-V interval duration, and $T_{n-1}$ is the previous value of the first indicated pacing interval.

Initialization of filter 515 includes seeding the filter by storing, in register 520, an initial interval value. In one embodiment, register 520 is initialized to an interval value corresponding to a lower rate limit (LRL), i.e., a minimum rate at which pacing pulses are delivered by device 105. Register 520 could alternatively be initialized with any other suitable value.

Filter Example 2

In one embodiment, operation of filter 515 is based on whether the beat concluding the most recent V-V interval $VV_n$ is a sensed/intrinsic beat or a paced/evoked beat. In this embodiment, the pacing control module 505, which controls the timing and delivery of pacing pulses, provides an input to filter 515 that indicates whether the most recent V-V interval $VV_n$ was concluded by an evoked beat initiated by a pacing stimulus delivered by device 105, or was concluded by an intrinsic beat sensed by ventricular sensing circuit 310.

In general terms, if the most recent V-V interval $VV_n$ is concluded by a sensed/intrinsic beat, then filter 515 provides a new first indicated pacing interval $T_n$ that is adjusted from the value of the previous first indicated pacing interval $T_{n-1}$ such as, for example, decreased by an amount that is based at least partially on the duration of the most recent V-V interval $VV_n$ and on the duration of the previous value of the first indicated pacing interval $T_{n-1}$. If, however, the most recent V-V interval $VV_n$ is concluded by a paced/evoked beat, then filter 515 provides a new first indicated pacing interval $T_n$ that is increased from the value of the previous first indicated pacing interval $T_{n-1}$, such as, for example, by an amount that is based at least partially on the duration of the most recent V-V interval $VV_n$ and on the duration of the previous value of the first indicated pacing interval $T_{n-1}$. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$.

Figure 7:
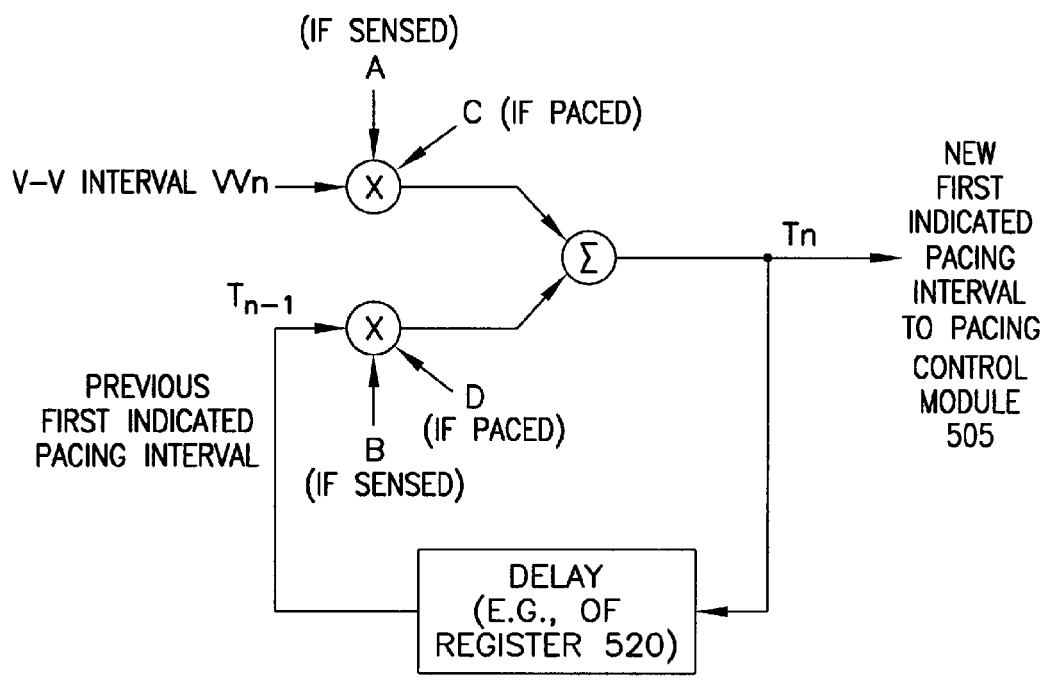
FIG. 7 is a signal flow diagram illustrating generally another conceptualization of operating the filter.

FIG. 7 is a signal flow diagram, illustrating generally, by way of example, but not by way of limitation, another conceptualization of operating filter 515, with certain differences from FIG. 6 more particularly described below. In this embodiment, the pacing control module 505, which controls the timing and delivery of pacing pulses, provides an input to filter 515 that indicates whether the most recent V-V interval $VV_n$ was concluded by an evoked beat initiated by a pacing stimulus delivered by device 105, or was concluded by an intrinsic beat sensed by ventricular sensing circuit 310.

If the most recent V-V interval $VV_n$ was concluded by an intrinsic beat, then the most recent V-V interval $VV_n$ and the previous value of the first indicated pacing interval $T_{n-1}$ are each scaled by respective constants A and B, and then summed to obtain the new value of the first indicated pacing interval $T_n$, which is stored in register 520 and provided to pacing control module 505. Alternatively, if the most recent V-V interval $VV_n$ was concluded by a evoked/paced beat, then the most recent V-V interval $VV_n$ and the previous value of the first indicated pacing interval $T_{n-1}$ are each scaled by respective constants C and D, and then summed to obtain the new value of the first indicated pacing interval $T_n$, which is stored in register 520 and provided to pacing control module 505. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 515 is described by $T_n = A \cdot VV_n + B \cdot T_{n-1}$, if $VV_n$ is concluded by an intrinsic beat, and is described by $T_n = C \cdot VV_n + D \cdot T_{n-1}$, if $VV_n$ is concluded by a paced beat, where A, B, C and D are coefficients (also referred to as "weights"), $VV_n$ is the most recent V-V interval duration, $T_n$ is the new value of the first indicated pacing interval, and $T_{n-1}$ is the previous value of the first indicated pacing interval. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$.

Filter Example 3

Figure 8:
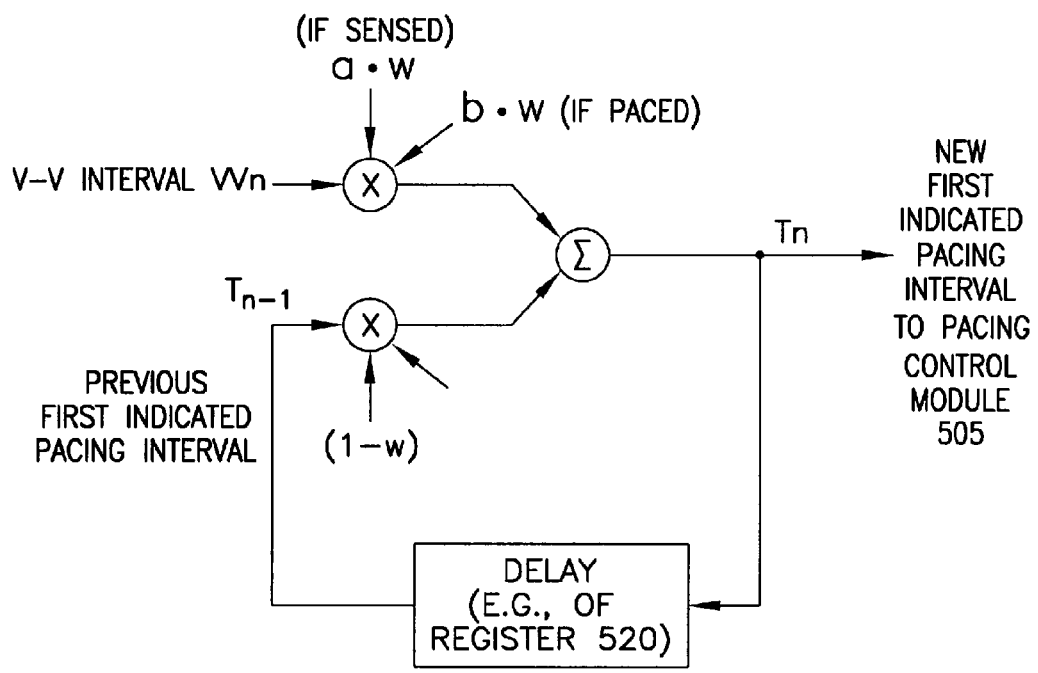
FIG. 8 is a signal flow diagram illustrating generally a further conceptualization of operating the filter.

In another embodiment, these coefficients can be more particularly described using an intrinsic coefficient (a), a paced coefficient (b), and a weighting coefficient (w). In one such embodiment, $A = a \cdot w$, $B = (1-w)$, $C = b \cdot w$, and $D = (1-w)$. In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \cdot VV_n + (1-w) \cdot T_{n-1}$, if $VV_n$ is concluded by a paced beat, as illustrated generally, by way of example, but not by way of limitation, in the signal flow graph of FIG. 8. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $VV_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent V-V interval $VV_n$ increases and the weighting effect of the previous first indicated pacing rate $T_{n-1}$ decreases. In one embodiment, $w = \frac{1}{16} = 0.0625$. In another embodiment, $w = \frac{1}{32}$. Another possible range for w is from $w = \frac{1}{2}$ to $w = \frac{1}{1024}$. A further possible range for w is from $w \approx 0$ to $w \approx 1$. Other values of w, which need not include division by powers of two, may be substituted without departing from the present method and apparatus.

In one embodiment, intrinsic coefficient a, is selected to be greater than 0.5, or to be greater than 1.0. In one example, the intrinsic coefficient a is selected to be lesser in value than the pacing coefficient b. In one example, $a \approx 1.1$ and $b \approx 1.2$. In another embodiment $a = 0.9$ and $b = 1.1$. One possible range for a is from $a = 0.5$ to $a = 2.0$, and for b is from $b = 1.0$ to $b = 3.0$. The coefficients may vary without departing from the present method and apparatus.

In one embodiment, for $b > 1$ and for substantially regular V-V intervals, filter 515 provides a new first indicated pacing interval $T_n$ that is at least slightly longer than the expected intrinsic V-V interval being measured by timer 515. Thus, if the intrinsic V-V interval being timed is consistent with the duration of previously received V-V intervals, then filter 515 avoids triggering a pacing stimulus. In such a case, a pacing pulse is delivered only if the presently timed V-V interval becomes longer than the previous substantially constant V-V intervals. In general terms, filter 515 operates so that pacing pulses are typically inhibited if the ventricular rate is substantially constant. However, if the measured V-V intervals become irregular, then filter 515 operates, over a period of one or several such V-V intervals, to shorten the first indicated pacing interval $T_n$ so that pacing stimuli are being delivered.

According to one aspect of the invention, it is believed that if the irregular V-V intervals are caused by a conducted atrial tachyarrhythmia, then pacing the ventricle will regularize the ventricular heart rate by establishing retrograde conduction from the ventricle. This, in turn, blocks forward conduction of atrial signals through the atrioventricular (A-V) node. As a result, irregular atrial signals do not trigger resulting irregular ventricular contractions. According to another aspect of the invention, however, this method and apparatus will not introduce pacing pulses until the heartbeat becomes irregular.

Therefore, the heart is assured to pace at its intrinsic rate when regular ventricular contractions are sensed.

Controller Example 2

Figure 9:
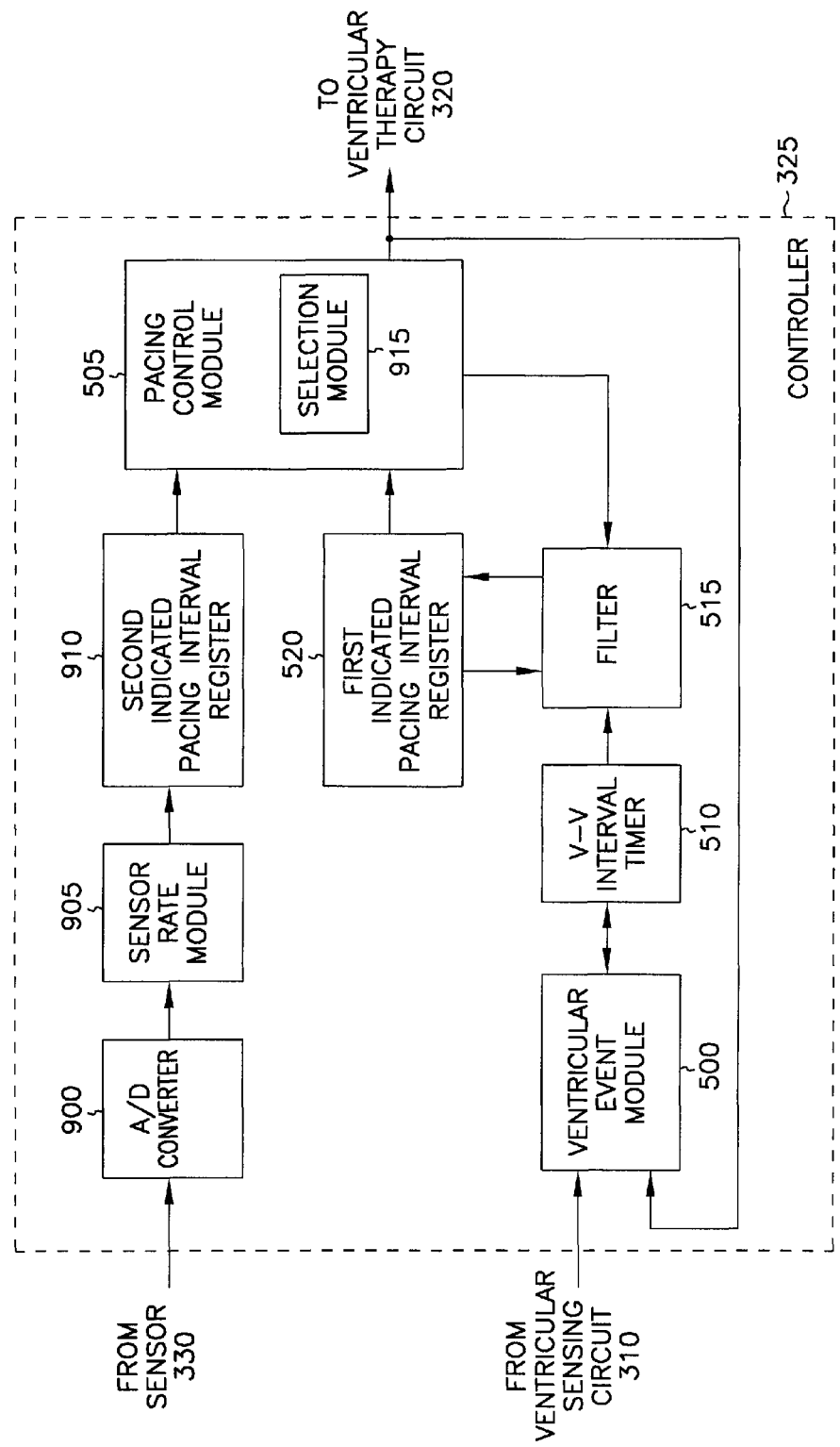
FIG. 9 is a schematic diagram illustrating generally another conceptualization of portions of a controller.

FIG. 9 is a schematic diagram illustrating generally, by way of example, but not by way of limitation, another conceptualization of portions of controller 325, with certain differences from FIG. 5 more particularly described below. In FIG. 9, controller 325 receives from sensor 330 a signal including information from which a physiologically desired heart rate (e.g., based on the patient's activity, respiration, or any other suitable indicator of metabolic need) can be derived. The sensor signal is digitized by an A/D converter 900. The digitized signal is processed by a sensor rate module 905, which computes a desired heart rate that is expressed in terms of a second indicated pacing interval stored in register 910.

Pacing control module 505 delivers a control signal, which directs ventricular therapy circuit 320 to deliver a pacing pulse, based on either (or both) of the first or second indicated pacing intervals, stored in registers 520 and 910, respectively, or both. In one embodiment, pacing control module 505 includes a selection module 915 that selects between the new first indicated pacing interval $T_n$ and the sensor-based second indicated pacing interval.

In one embodiment, selection module 915 selects the shorter of the first and second indicated pacing intervals as the selected indicated pacing interval $S_n$. If no ventricular beat is sensed during the selected indicated pacing interval $S_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the selected indicated pacing interval $S_n$.

In general terms, for this embodiment, the ventricle is paced at the higher of the sensor indicated rate and the VRR indicated rate. If, for example, the patient is resting, such that the sensor indicated rate is lower than the patient's intrinsic rate, and the patient's intrinsic rate is substantially constant, then the intrinsic rate is higher than the VRR indicated rate. As a result, pacing pulses generally will not be delivered. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate. In an alternative embodiment, the pacing rate is determined by blending the sensor indicated rate and the VRR indicated rate, rather than by selecting the higher of these two indicated rates (i.e., the shorter of the first and second indicated pacing intervals).

In another embodiment, selection module 915 provides a selected indicated pacing interval $S_n$ based on a blending of both the first and second indicated pacing intervals. In one such example, selection module 915 applies predetermined or other weights to the first and second indicated pacing intervals to compute the selected pacing interval $S_n$.

Controller Example 2

Figure 10:
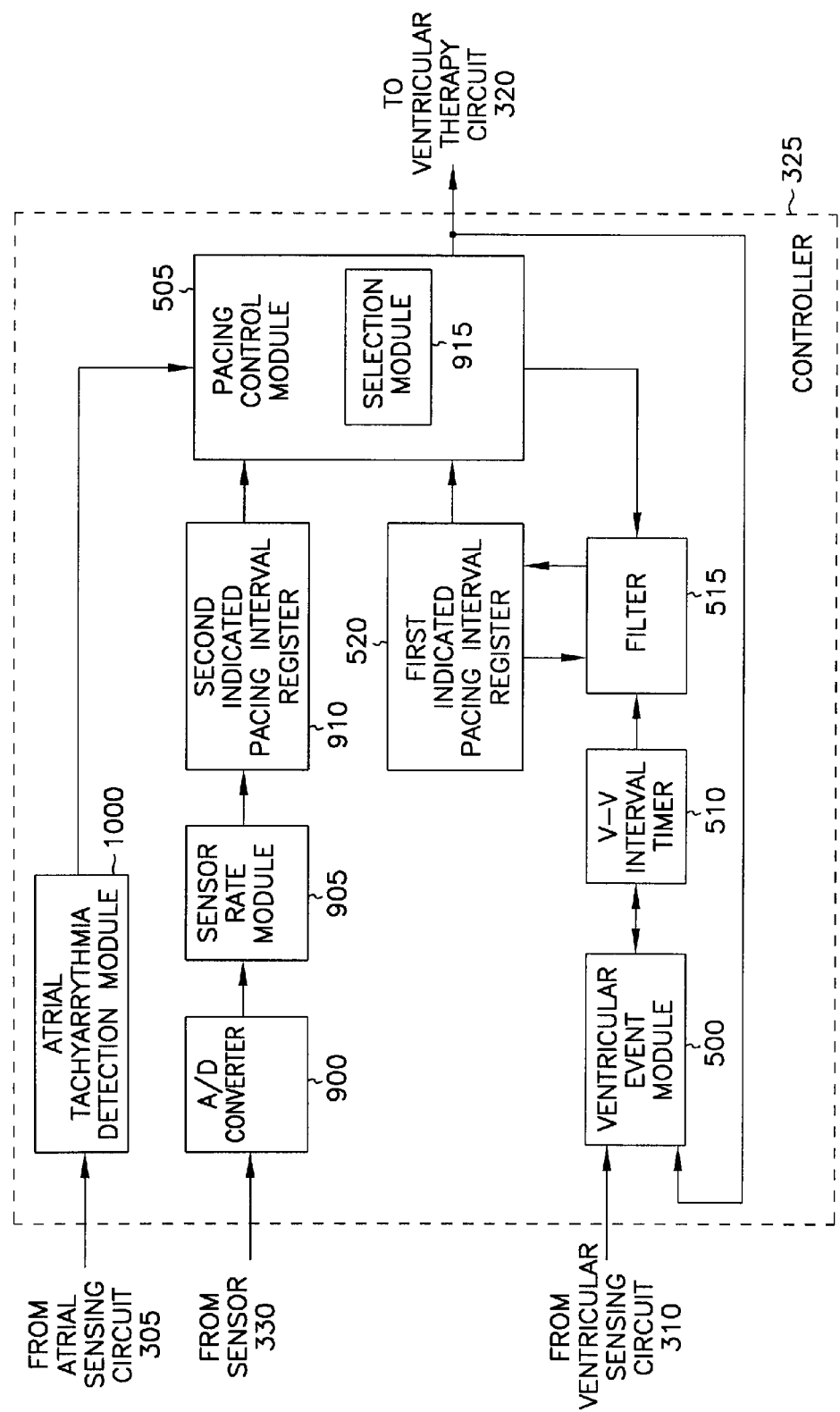
FIG. 10 is a schematic diagram illustrating generally a further conceptualization of portions of a controller.

FIG. 10 is a schematic diagram illustrating generally, by way of example, but not by way of limitation, another conceptualization of portions of controller 325, with certain differences from FIG. 9 more particularly described below. In FIG. 10, controller 325 includes an atrial tachyarrhythmia (AT) detection module 1000 that receives a signal from atrial sensing circuit 305. The received signal includes information about atrial events, from which AT detection module 1000 determines the presence or absence of one or more atrial tachyarrhythmias, such as atrial fibrillation.

In one embodiment, AT detection module 1000 provides a control signal, to pacing control module 505, that indicates the presence or absence of an atrial tachyarrhythmia, such as atrial fibrillation. In one embodiment, selection module 915 selects between the first and second indicated pacing intervals as illustrated, by way of example, but not by way of limitation, in Table 1.

TABLE 1

Example Selection Based on AT Detection, 1st Indicated Pacing Interval, and 2nd Indicated Pacing Interval

| AT Present? | 1st Indicated Pacing Interval < 2nd Indicated Pacing Interval? | 1st Indicated Pacing Interval ≧ 2nd Indicated Pacing Interval? |
|---|---|---|
| Yes, AT Present | $S_n$ ← 1st Indicated Pacing Interval (i.e., VRR) | $S_n$ ← 2nd Indicated Pacing Interval (e.g., Sensor) |
| No, AT not Present | $S_n$ ← 2nd Indicated Pacing Interval (e.g., Sensor) | $S_n$ ← 2nd Indicated Pacing Interval (e.g., Sensor) |

In this embodiment, if an atrial tachyarrhythmia is present and the first indicated pacing interval is shorter than the second indicated pacing interval, then selection module 915 selects the first indicated pacing interval, which is based on the VRR techniques described above, as the selected indicated pacing interval $S_n$. Otherwise, selection module 915 selects the second indicated pacing interval, which in one embodiment is based on the sensor indications, as the selected indicated pacing interval $S_n$. As discussed above, if no ventricular beat is sensed during the selected indicated pacing interval $S_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the selected indicated pacing interval $S_n$.

Stated differently, for this embodiment, the ventricle is paced at the VRR indicated rate only if an atrial tachyarrhythmia, such as atrial fibrillation, is present and the VRR indicated rate exceeds the sensor indicated rate. Otherwise the ventricle is paced at the sensor indicated rate. If, for example, the patient is resting, such that the sensor indicated rate is lower than the patient's intrinsic rate, and no atrial tachyarrhythmia is present, then the device will sense the intrinsic rate or will deliver ventricular paces at the lower rate limit. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate, whether or not atrial tachyarrhythmia is present. As an alternative to the selection described with respect to Table 1, selection module 915 provides a fixed or variable weighting or blending of both the sensor-indicated rate and VRR indicated rate, such that pacing pulses are delivered based on the blended rate.

The second indicated pacing interval need not be based on sensor indications. In one embodiment, for example, the second indicated pacing interval tracks the sensed atrial heart rate when no atrial tachyarrhythmia is present. In this embodiment, selection module 915 performs a mode-switching function in which the first indicated pacing interval is used whenever atrial tachyarrhythmia is present and the second indicated pacing interval (e.g., atrial-tracking) is used when no atrial tachyarrhythmia is present.

In another embodiment, heart rate/interval is used as a trigger turn on/off use of the first indicated pacing interval (e.g., the VRR indicated pacing interval). In one example, pacing therapy is based on the first indicated pacing interval if the first indicated pacing interval is longer than a first predetermined value, and pacing therapy is substantially independent of the first indicated pacing interval if the first indicated pacing interval is shorter than the first predetermined value. In this example, the VRR indicated pacing interval is used at low heart rates, but not at fast heart rates.

Filter Rate Behavior Example 1

Figure 11:
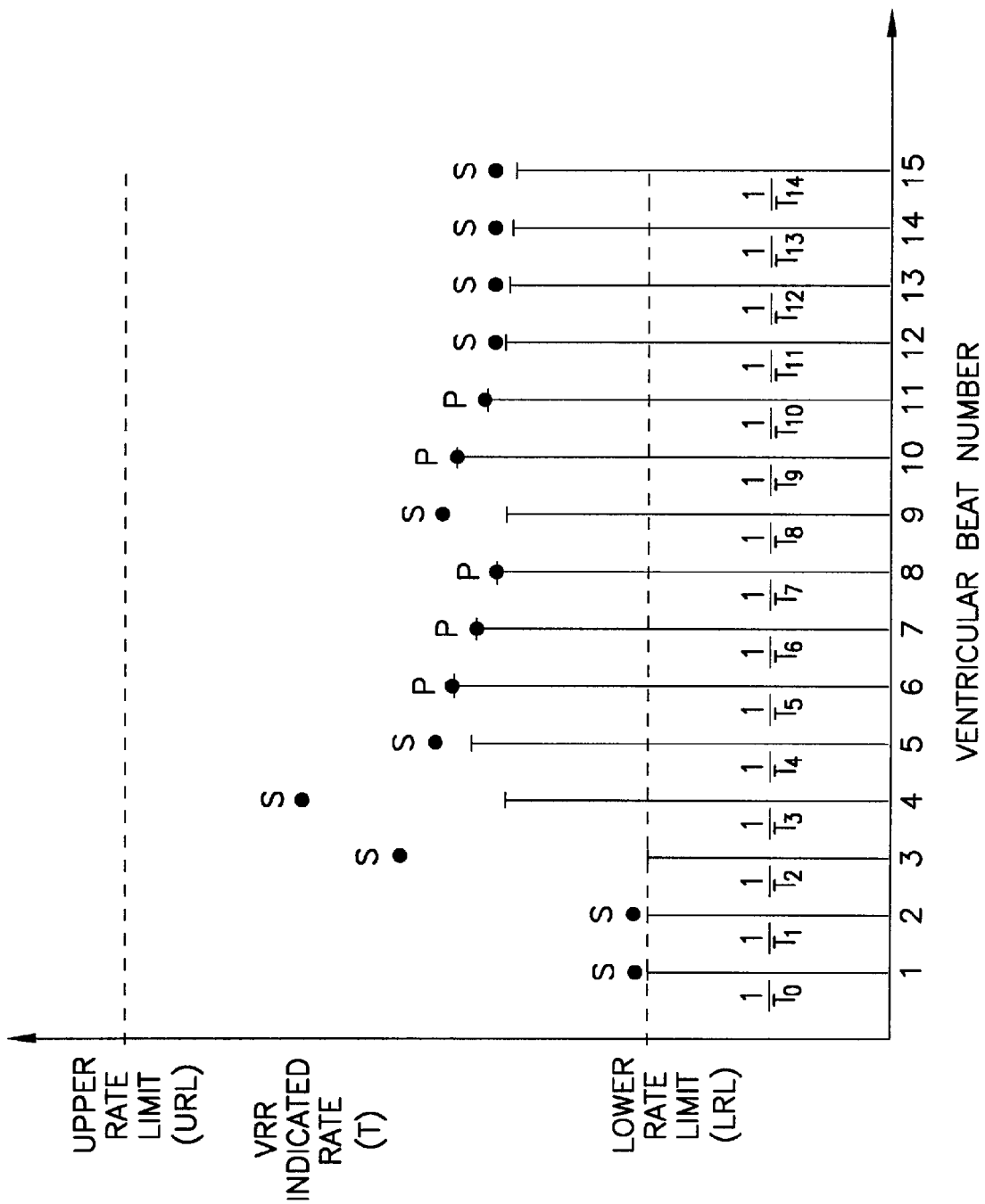
FIG. 11 is a graph illustrating generally one embodiment of operating a filter to provide a first indicated pacing rate, such as a VRR indicated rate, for successive ventricular heart beats.

FIG. 11 is a graph illustrating generally, by way of example, but not by way of limitation, one embodiment of a VRR indicated rate for successive ventricular heart beats for one mode of operating filter 515. As discussed above, the VRR indicated rate is simply the frequency, between ventricular heart beats, associated with the first indicated pacing interval. Stated differently, the VRR indicated rate is the inverse of the duration of the first indicated pacing interval. If pacing is based solely on the VRR indicated rate, pacing control module 505 directs ventricular therapy circuit 320 to issue a pacing pulse after the time since the last ventricular beat equals or exceeds the first indicated pacing interval. However, as described above, in certain embodiments, pacing control module 505 directs ventricular therapy circuit 320 to issue a pacing pulse based on factors other than the VRR indicated rate such as for, example, based on the sensor indicated rate.

In the example illustrated in FIG. 11, a first sensed intrinsic ventricular beat, indicated by an "S" was detected just before expiration of the first indicated pacing interval ("VRR indicated pacing interval") $T_0$, as computed based on a previous ventricular beat. In one embodiment, the new VRR indicated pacing interval $T_1$ is computed based on the duration of most recent V-V interval $VV_1$ and a previous value of the VRR indicated pacing interval $T_0$, as discussed above. In this example, the new VRR indicated pacing interval $T_1$ corresponds to a lower rate limit (LRL) time interval. In one embodiment, the allowable range of the VRR indicated pacing interval is limited so that the VRR indicated pacing interval does not exceed the duration of the LRL time interval, and so that the VRR indicated pacing interval is not shorter than the duration of an upper rate limit (URL) time interval.

The second ventricular beat is also sensed, just before expiration of the VRR indicated pacing interval $T_1$. In one embodiment, the new VRR indicated pacing interval $T_2$ is computed based on duration of most recent V-V interval $VV_2$ and a previous value of the VRR indicated pacing interval, $T_1$, as discussed above. The first and second ventricular beats represent a stable intrinsic rhythm, for which no pacing is delivered because the VRR indicated pacing interval is at a lower rate than the sensed intrinsic ventricular beats.

The third, fourth, and fifth ventricular beats represent the onset of atrial fibrillation, resulting in erratic ventricular rates. The third ventricular beat is sensed well before expiration of the VRR indicated pacing interval $T_2$, such that no pacing pulse is issued. For the sensed third ventricular beat, filter 515 computes the new VRR indicated pacing interval $T_3$ as being shorter in duration relative to the previous VRR indicated pacing interval $T_2$.

The fourth ventricular beat is similarly sensed well before expiration of the VRR indicated pacing interval $T_3$, such that no pacing pulse is issued. For the sensed fourth ventricular beat, filter 515 computes the new VRR indicated pacing interval $T_4$ as being shorter in duration relative to the previous VRR indicated pacing interval $T_3$.

The fifth ventricular beat is sensed before expiration of the VRR indicated pacing interval $T_4$, such that no pacing pulse is issued. For the sensed fifth ventricular beat, filter 515 computes the new VRR indicated pacing interval $T_5$ as being shorter in duration relative to the previous VRR indicated pacing interval $T_4$.

The sixth, seventh, and eighth ventricular beats indicate regularization of the ventricular rate using the pacing techniques described above. No ventricular beat is sensed during the VRR indicated pacing interval $T_5$, so a pacing pulse is issued to evoke the sixth ventricular beat. A new VRR indicated pacing interval $T_6$ is computed as being increased in duration relative to the previous VRR indicated pacing interval $T_5$, lowering the VRR indicated rate. Similarly, no ventricular beat is sensed during the VRR indicated pacing interval.

The ninth ventricular beat represents another erratic ventricular beat resulting from the atrial fibrillation episode. The ninth ventricular beat is sensed before expiration of the VRR indicated pacing interval $T_8$. As a result, a shorter new VRR indicated pacing interval $T_9$ is computed.

The tenth and eleventh ventricular beats illustrate further regularization of the ventricular rate using the pacing techniques described above. No ventricular beat is sensed during the VRR indicated pacing interval $T_9$, so a pacing pulse is issued to evoke the tenth ventricular beat. A new VRR indicated pacing interval $T_{10}$ is computed as being increased in duration relative to the previous VRR indicated pacing interval $T_9$, lowering the VRR indicated rate. Similarly, no ventricular beat is sensed during the VRR indicated pacing interval $T_{10}$, so a pacing pulse is issued to evoke the tenth ventricular beat. A new VRR indicated pacing interval $T_{11}$ is compute as being increased in duration relative to the previous VRR indicated pacing interval $T_{10}$, lowering the VRR indicated rate.

The twelfth, thirteenth, fourteenth, and fifteenth ventricular beats illustrate resumption of a stable intrinsic rhythm after termination of the atrial fibrillation episode. For such a stable rate, the VRR indicated rate proceeds asymptotically toward a "floor value" that tracks, but remains below, the intrinsic rate. This allows the intrinsic heart signals to control heart rate when such intrinsic heart signals provide a stable rhythm. As a result, when the patient's intrinsic rate is constant, paces will be withheld, allowing the patient's intrinsic heart rhythm to continue. If the patient's heart rate includes some variability, and the VRR indicated floor value is close to the mean intrinsic heart rate, then occasional paced beats will occur. Such pace beats will gradually lengthen the VRR indicated pacing interval, thereby allowing subsequent intrinsic behavior when the patient's heart rate becomes substantially constant.

The intrinsic coefficient a of filter 515 controls the "attack slope" of the VRR indicated heart rate as the VRR indicated heart rate increases because of sensed intrinsic beats. The paced coefficient b of filter 515 controls the "decay slope" of the VRR indicated heart rate as the VRR indicated heart rate decreases during periods of paced beats. In one embodiment, in which a>1.0 and b>1.0, decreasing the value of a toward 1.0 increases the attack slope such that the VRR indicated rate increases faster in response to sensed intrinsic beats, while decreasing the value of b toward 1.0 decreases the decay slope such that the VRR indicated rate decreases more slowly during periods of paced beats. Conversely, for a>1.0 and b>1.0, increasing the value of a from 1.0 decreases the attack slope such that the VRR indicated rate increases more slowly in response to sensed intrinsic beats, while increasing the value of b from 1.0 increases the decay slope such that the VRR-indicated rate decreases more quickly during periods of paced beats.

In one embodiment, for a>1.0 and b>1.0, decreasing both a and b toward 1.0 increases VRR indicated rate during periods of sensed intrinsic activity so that the VRR indicated rate is closer to the mean intrinsic rate. Because the VRR indicated rate is closer to the mean intrinsic rate, variability in the intrinsic heart rate is more likely to trigger paces at the VRR indicated rate. On the other hand, for a>1.0 and b>1.0, increasing both a and b from 1.0 decreases the VRR indicated rate during periods of sensed intrinsic activity so that the VRR indicated rate is farther beneath the mean intrinsic rate. Because the VRR indicated rate is farther beneath the mean intrinsic rate, the same variability in the intrinsic heart rate becomes less likely to trigger paces at the VRR indicated rate.

In one embodiment, these coefficients are programmable by the user, such as by using remote programmer 125. In another embodiment, the user selects a desired performance parameter (e.g., desired degree of rate regularization, desired attack slope, desired decay slope, etc.) from a corresponding range of possible values, and device 105 automatically selects the appropriate combination of coefficients of filter 515 to provide a filter setting that corresponds to the selected user-programmed performance parameter, as illustrated generally by Table 2. Other levels of programmability or different combinations of coefficients may also be used.

TABLE 2

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Rate Regularization) | 2.0 | 3.0 |
| 2 | 1.8 | 2.6 |
| 3 | 1.6 | 2.2 |
| 4 | 1.4 | 1.8 |
| 5 | 1.2 | 1.4 |
| 6 (More Rate Regularization) | 1.0 | 1.0 |

Filter Rate Behavior Example 2

Figure 12:
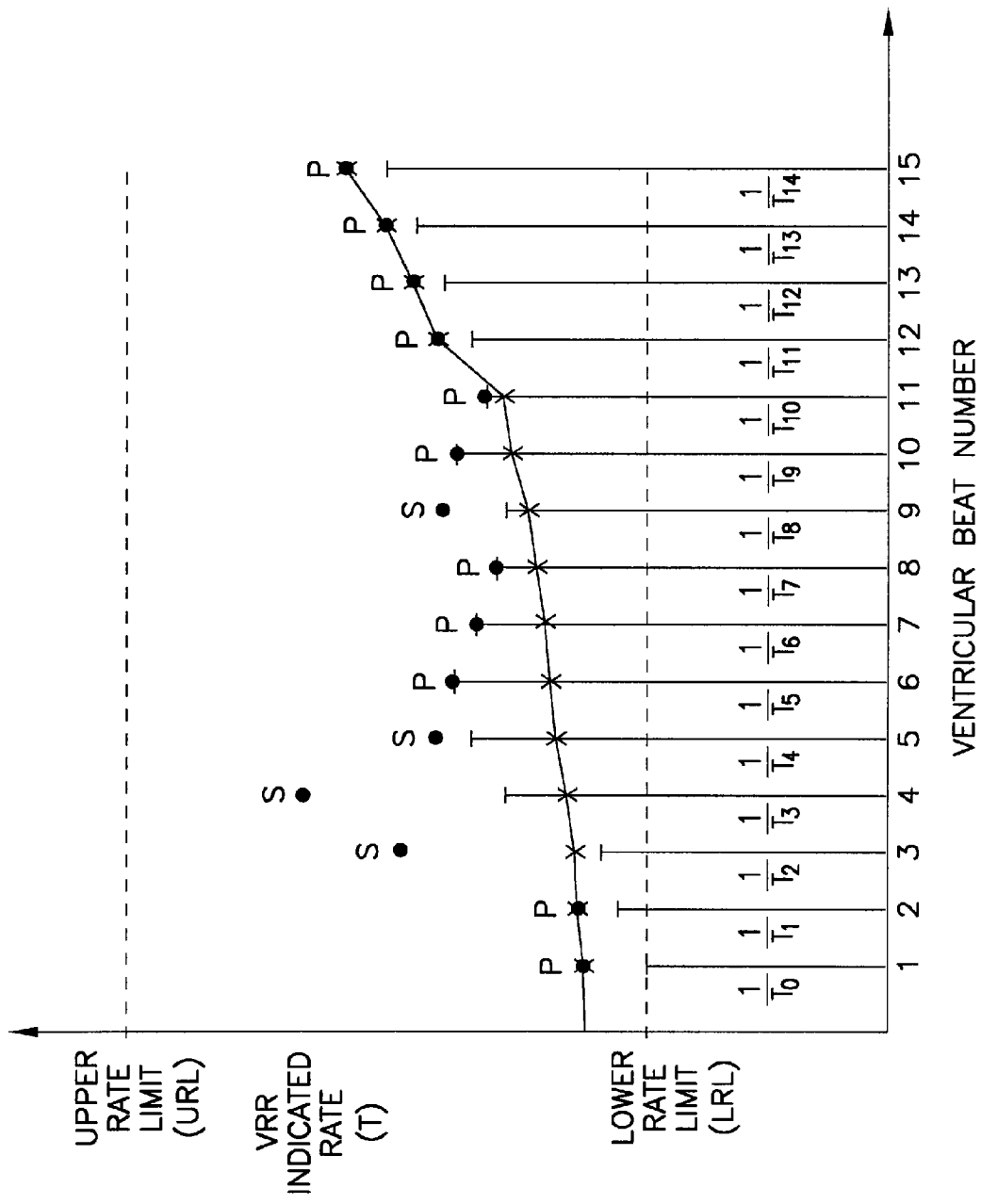
FIG. 12 is a graph illustrating generally another embodiment of operating a filter to provide the first indicated pacing rate, such as a VRR indicated rate, and delivering therapy based on the first indicated pacing rate and based on a second indicated pacing rate, such as a sensor indicated rate.

FIG. 12 is a graph illustrating generally, by way of example, but not by way of limitation, one embodiment of selecting between more than one indicated pacing interval. FIG. 12 is similar to FIG. 11 in some respects, but FIG. 12 includes a second indicated pacing interval. In one embodiment, the first indicated pacing interval is the VRR indicated pacing interval, described above, and the second indicated pacing interval is a sensor indicated pacing interval, from an accelerometer, minute ventilation, or other indication of the patient's physiological need for increased cardiac output.

In one embodiment, a selected indicated pacing interval is based on the shorter of the first and second indicated pacing intervals. Stated differently, device 105 provides pacing pulses at the higher indicated pacing rate. In the example illustrated in FIG. 12, first and second beats and the twelfth through fifteenth beats are paced at the sensor indicated rate, because it is higher than the VRR indicated rate and the intrinsic rate. The third, fourth, fifth, and ninth beats are sensed intrinsic beats that are sensed during the shorter of either of the VRR and sensor indicated pacing intervals. The sixth through eighth beats and tenth and eleventh beats are paced at the VRR indicated rate, because it is higher than the sensor indicated rate. Also, for these beats, no intrinsic beats are sensed during the VRR indicated intervals. In one embodiment, the above-described equations for filter 515 operate to increase the VRR indicated rate toward the sensor-indicated rate when the sensor indicated rate is greater than the VRR indicated rate, as illustrated by first through third and twelfth through fifteenth beats in FIG. 12. In an alternate embodiment, however, $T_n = b \cdot w \cdot VV_n + (1-w) \cdot T_{n-1}$, if $VV_n$ is concluded by a VRR indicated paced beat, and $T_n = T_{n-1}$ if $VV_n$ is concluded by a sensor indicated paced beat, thereby leaving the VRR indicated rate unchanged for sensor indicated paced beats.

In this embodiment, the ranges of both the sensor indicated rate and the VRR indicated rate are limited so that they do not extend to rates higher than the URL or to rates lower than the LRL. In one embodiment, the LRL and the URL are programmable by the user, such as by using remote programmer 125.

In a further embodiment, the selected indicated pacing interval is based on the shorter of the first and second indicated pacing intervals only if an atrial tachyarrhythmia, such as atrial fibrillation, is present. Otherwise, the second indicated pacing interval is used, as described above.

Filter Rate Behavior Example 3

Figure 13:
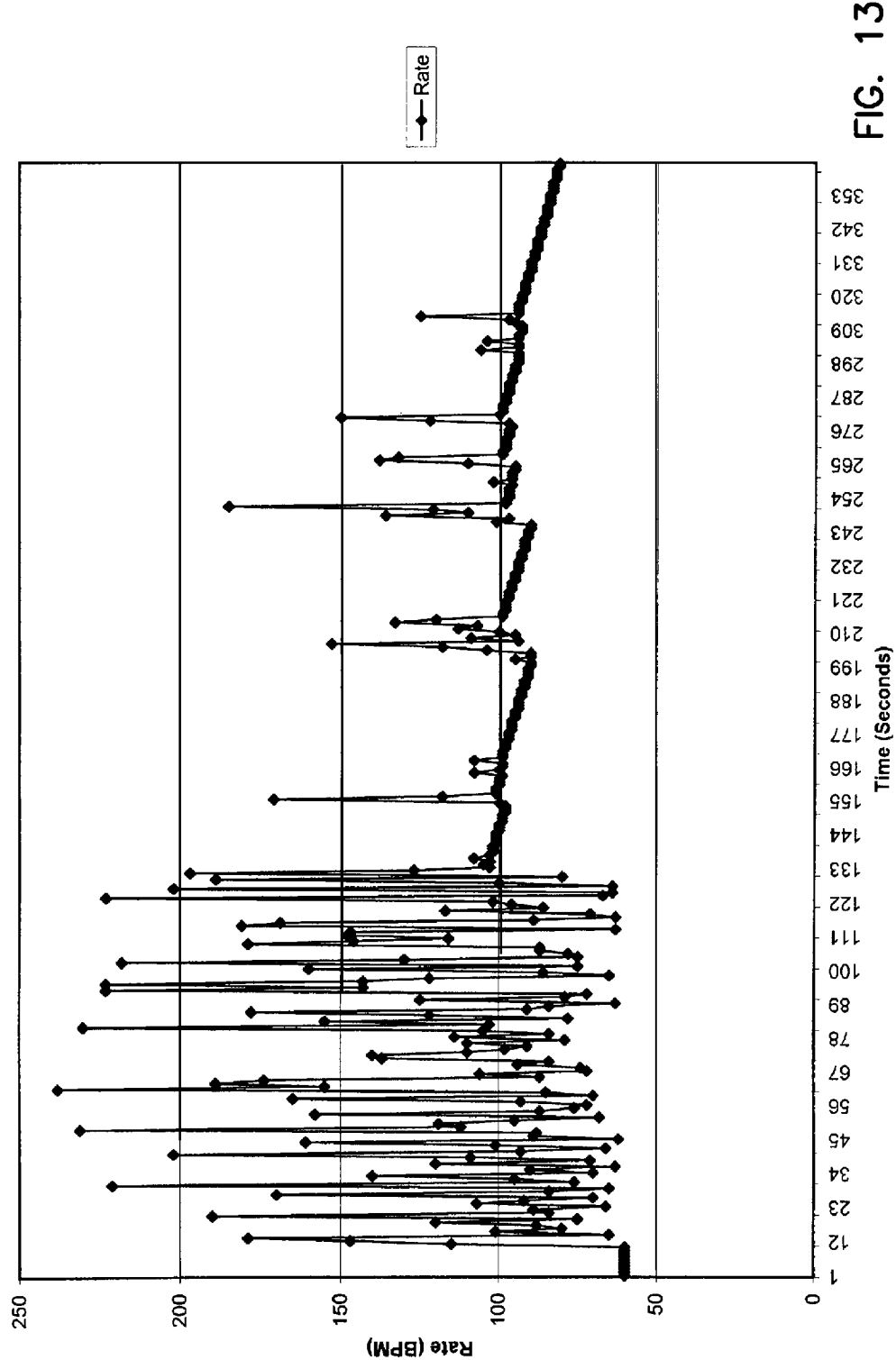
FIG. 13 is a graph illustrating generally another illustrative example of heart rate vs. time according to a VRR algorithm spreadsheet simulation.

FIG. 13 is a graph illustrating generally, by way of example, but not by way of limitation, another illustrative example of heart rate vs. time according to a spreadsheet simulation of the behavior of the above-described VRR algorithm. In FIG. 13, the VRR algorithm is turned off until time 130. Stable intrinsic lower rate behavior is modeled for times between 0 and 10 seconds. Erratic intrinsic ventricular rates, such as would result from atrial tachyarrhythmias including atrial fibrillation, are modeled during times between 10 seconds and 130 seconds. At time 130 seconds, the VRR algorithm is turned on. While some erratic intrinsic beats are subsequently observed, the VRR algorithm provides pacing that is expected to substantially stabilize the heart rate, as illustrated in FIG. 13. The VRR indicated pacing rate gradually decreases until intrinsic beats are sensed, which results in a slight increase in the VRR indicated pacing rate. Thus, the VRR algorithm favors the patient's intrinsic heart rate when it is stable, and paces at the VRR indicated heart rate when the patient's intrinsic heart rate is unstable. It is noted that FIG. 13 does not represent clinical data, but rather provides a simulation model that illustrates one example of how the VRR algorithm is expected to operate.

Filter Example 4

In one embodiment, filter 515 includes variable coefficients such as, for example, coefficients that are a function of heart rate (or its corresponding time interval). In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \cdot VV_n + (1-w) \cdot T_{n-1}$, if $VV_n$ is concluded by a paced beat, where at least one of a and b are linear, piecewise linear, or nonlinear functions of one or more previous V-V intervals such as, for example, the most recent V-V interval, $VV_n$.

Figure 14:
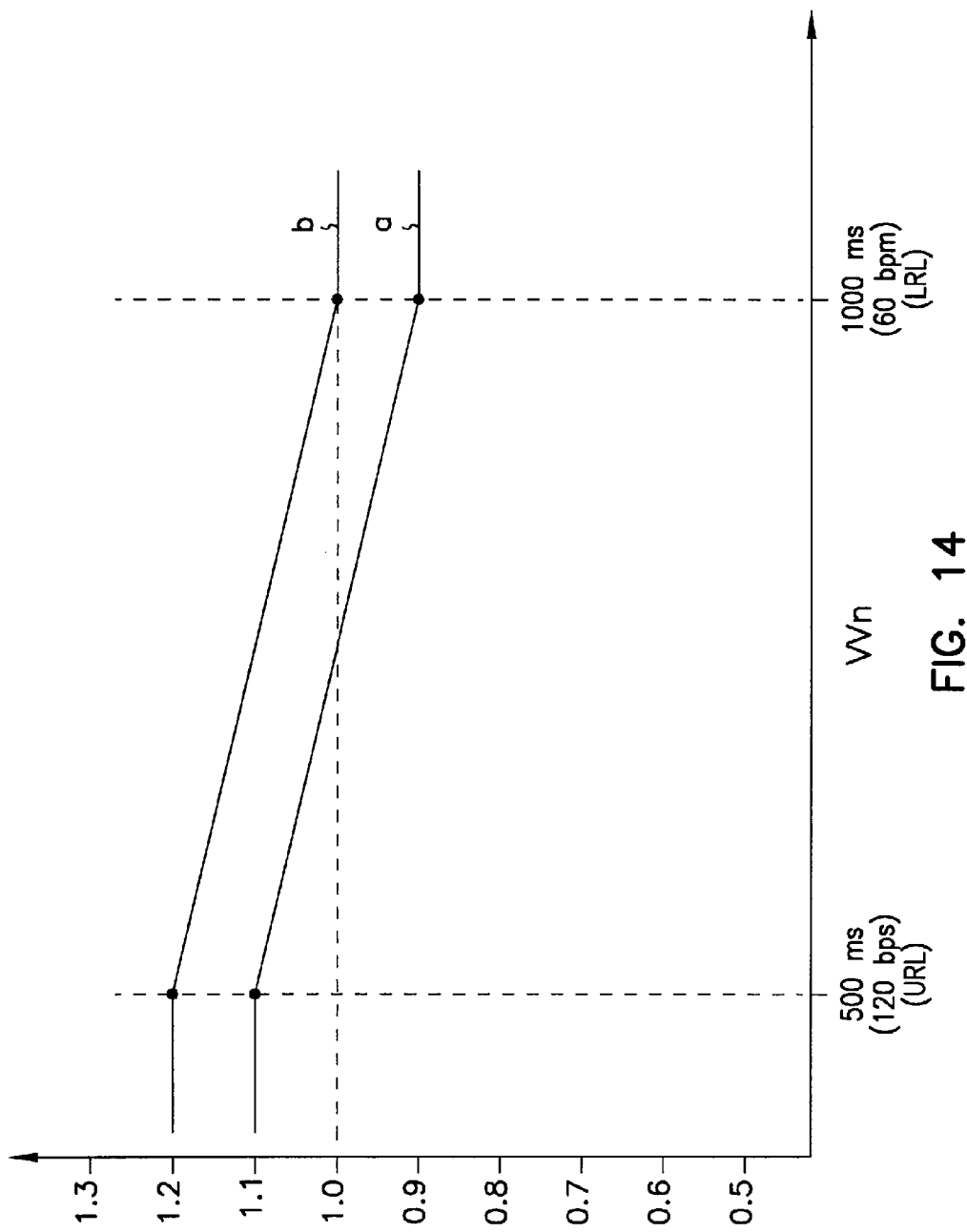
FIG. 14 is a graph illustrating generally one embodiment of using at least one of coefficients a and b as a function of heart rate (or a corresponding time interval).

FIG. 14 is a graph illustrating generally, by way of example, but not by way of limitation, one embodiment of using at least one of coefficients a and b as a function of one or more previous V-V intervals such as, for example, the most recent V-V interval $VV_n$. In one such example, a is less than 1.0 when $VV_n$ is at or near the lower rate limit (e.g., 1000 millisecond interval or 60 beats/minute), and a is greater than 1.0 when $VV_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $VV_n$ is at or near the lower rate limit, and b is greater than 1.0 when $VV_n$ is at or near the upper rate limit. For a constant a, using a smaller value of b at lower rates will decrease the pacing rate more slowly for paced events; using a larger value of b at higher rates decreases the pacing rate more quickly for paced events.

CONCLUSION

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system comprising:
a ventricular sensing circuit configured to sense ventricular beats;
a storage element configured for storing a computed V-V interval duration;
a controller, including or coupled to the storage element configured for storing a computed V-V interval duration, the controller coupled to the ventricular sensing circuit, wherein the controller is configured to obtain V-V intervals between the ventricular beats and to compute a first indicated pacing interval including summing a first addend that is determined using a weighted most recent V-V interval duration and a second addend that is determined using an equally or differently weighted previous first indicated pacing interval;
a ventricular therapy circuit, coupled to the controller, configured to provide pacing therapy using the first indicated pacing interval; and
wherein the controller is configured to decrease the first pacing interval following an intrinsic ventricular beat.

2. The system of claim 1, wherein the controller is configured to increase the first pacing interval following a paced ventricular beat.

3. The system of claim 1, wherein the previous first indicated pacing interval consists of the first indicated pacing interval directly preceding the most recent V-V interval duration.

4. The system of claim 1, wherein the controller is configured to weight at least one of the first addend and the second addend using information from one or more previous V-V intervals.

5. The system of claim 4, wherein the controller is configured to weight at least one of the first addend and the second addend using information from at least one of a most recent ventricular beat of the most recent V-V interval duration and a most recent ventricular beat of the stored previous first indicated pacing interval.

6. The system of claim 5, wherein the information from the most recent ventricular beat includes whether the most recent ventricular beat includes an intrinsic ventricular beat or a paced ventricular beat.

7. The system of claim 1, wherein the controller is configured to compute the first indicated pacing interval $(T_n)$ according to: $T_n = a \cdot w \cdot VV_n + (1-w) \cdot T_{n-1}$, if $VV_n$ is concluded by an intrinsic beat, wherein a and w are coefficients, otherwise $T_n$ is computed according to: $T_n = b \cdot w \cdot VV_n + (1-w) \cdot T_{n-1}$, if $VV_n$ is concluded by a paced beat, wherein b and w are coefficients.

8. The system of claim 7, wherein at least one of a, b, and w is a function of heart rate.

9. The system of claim 1, including:
a sensor, coupled to the controller, configured to sense a physiological signal;
wherein the controller is configured to compute a second indicated pacing interval using the physiological signal; and
wherein the ventricular therapy circuit is configured to provide pacing therapy using the second indicated pacing interval.

10. The system of claim 1, wherein the controller is configured to compute a first indicated pacing interval by summing a first addend that includes a most recent V-V interval duration with a second addend that includes a stored previously-computed value of the first indicated pacing interval.

11. The system of claim 10, wherein the stored previously-computed value of the first indicated pacing interval consists of the directly preceding first indicated pacing interval.

12. A system comprising:
means for sensing ventricular beats;
means for obtaining V-V intervals between the ventricular beats;
means for computing a first indicated pacing interval including summing a first addend with a second addend, including determining the first addend using a weighted most recent V-V interval duration and determining the second addend using an equally or differently weighted previous first indicated pacing interval;
means for providing pacing therapy using the first indicated pacing interval; and
means for decreasing the first pacing interval following an intrinsic ventricular beat.

13. A method comprising:
sensing ventricular beats;
obtaining V-V intervals between the ventricular beats;
computing a first indicated pacing interval including summing a first addend with a second addend, including determining the first addend using a weighted most recent V-V interval duration and determining the second addend using an equally or differently weighted previous first indicated pacing interval;
providing pacing therapy using the first indicated pacing interval; and
decreasing the first pacing interval following an intrinsic ventricular beat.

14. The method of claim 13, including increasing the first pacing interval following a paced ventricular beat.

15. The method of claim 13, wherein the previous first indicated pacing interval consists of the first indicated pacing interval directly preceding the most recent V-V interval duration.

16. The method of claim 13, including weighting at least one of the first addend and the second addend using information from one or more previous V-V intervals.

17. The method of claim 13, including weighting at least one of the first addend and the second addend using information from at least one of a most recent ventricular beat of the most recent V-V interval duration and a most recent ventricular beat of a stored previously-computed V-V interval duration.

18. The method of claim 17, wherein using information from the most recent ventricular beat includes using whether the most recent ventricular beat includes an intrinsic ventricular beat or a paced ventricular beat.

19. The method of claim 13, wherein computing the first indicated pacing interval ($T_n$) includes computing $T_n$ according to: $T_n = a \cdot w \cdot VV_n + (1-w) \cdot T_{n-1}$, if $VV_n$ is concluded by an intrinsic beat, wherein a and w are coefficients, otherwise computing $T_n$ includes computing $T_n$ according to: $T_n = b \cdot w \cdot VV_n + (1-w) \cdot T_{n-1}$, if $VV_n$ is concluded by a paced beat, wherein b and w are coefficients.

20. The method of claim 19, wherein at least one of a, b, and w is a function of heart rate.

21. The method of claim 13, including:
sensing a physiological signal;
computing a second indicated pacing interval using the physiological signal; and
providing pacing therapy using the second indicated pacing interval.

22. The method of claim 13, wherein computing a first indicated pacing interval includes by summing a first addend that includes a most recent V-V interval duration with a second addend that includes a stored previously-computed value of the first indicated pacing interval.

23. The method of claim 22, wherein the stored previously-computed value of the first indicated pacing interval consists of the directly preceding first indicated pacing interval.

* * * * *